(12) United States Patent
Choi et al.

(10) Patent No.: US 9,504,724 B2
(45) Date of Patent: Nov. 29, 2016

(54) **PHARMACEUTICAL COMPOSITION COMPRISING EXTRACT OF *PUERARIAE FLOS* FOR PREVENTION AND TREATMENT OF ENDOMETRIOSIS**

(71) Applicant: UNIVERSITY-INDUSTRY COOPERATION GROUP OF KYUNG HEE UNIVERSITY, Gyeonggi-do (KR)

(72) Inventors: Jung-Hye Choi, Seoul (KR); Ji-Hyyun Kim, Seoul (KR)

(73) Assignee: University-Industry Cooperation Group of Kyung-Hee University (KR)

( * ) Notice: Subject to any disclaimer, the term of this patent is extended or adjusted under 35 U.S.C. 154(b) by 0 days.

(21) Appl. No.: 14/346,667

(22) PCT Filed: Sep. 24, 2012

(86) PCT No.: PCT/KR2012/007653
§ 371 (c)(1),
(2) Date: Mar. 21, 2014

(87) PCT Pub. No.: WO2013/043011
PCT Pub. Date: Mar. 28, 2013

(65) Prior Publication Data
US 2014/0234451 A1    Aug. 21, 2014

(30) Foreign Application Priority Data
Sep. 23, 2011    (KR) .................. 10-2011-0096323

(51) Int. Cl.
*A61K 36/488*    (2006.01)

(52) U.S. Cl.
CPC ............ *A61K 36/488* (2013.01); *A23L 33/105* (2016.08)

(58) Field of Classification Search
None
See application file for complete search history.

(56) References Cited

U.S. PATENT DOCUMENTS

2009/0068299 A1 * 3/2009 Cohen ..................... 424/757

FOREIGN PATENT DOCUMENTS

| CN | 1133734 A | * | 10/1996 |
| KR | 10-2005-0038853 A | | 4/2005 |
| KR | 10-0540788 B1 | | 1/2006 |
| KR | 10-0547560 B1 | | 1/2006 |
| KR | 10-0552995 B1 | | 2/2006 |
| KR | 10-0950564 B1 | | 4/2010 |
| WO | WO 2007-110241 A1 | | 10/2007 |
| WO | WO 2009-033103 A1 | | 3/2009 |

OTHER PUBLICATIONS

International Search Report prepared by the Korean Intellectual Property Office on Feb. 28, 2013, for International Application No. PCT/KR2012/007653.
So-Jung, Kim et al. "A Study on the Estrogenicity of Korean Arrowroot (*Pueraria thunbergiana*)," Journal of the Korean Society of Food Science and Nutrition. 2004, vol. 33, No. 1, pp. 16-21.

* cited by examiner

*Primary Examiner* — Terry A McKelvey
*Assistant Examiner* — Catheryne Chen
(74) *Attorney, Agent, or Firm* — Sheridan Ross P.C.

(57) ABSTRACT

The present invention relates to a pharmaceutical composition containing Puerariae Flos extracts as active ingredients for preventing or treating endometriosis and the complications thereof. More particularly, Puerariae Flos extracts exhibit the activity of inhibiting the migration and adhesion of endometriosis cells, inhibiting the expressions of MMP-2 and MMP-9, which are factors associated with migration and adhesion, inhibiting the expression of COX-2, which is a factor associated with pain, and inhibiting the expression of MCP-1, which is a cytokine associated with inflammation, and RANTES. Therefore, the Puerariae Flos extracts of the present invention can be effectively used as active ingredients for a pharmaceutical composition for preventing and treating endometriosis and the complications thereof, and for a health food.

14 Claims, 17 Drawing Sheets

PHARMACEUTICAL COMPOSITION COMPRISING EXTRACT OF *PUERARIAE FLOS* FOR PREVENTION AND TREATMENT OF ENDOMETRIOSIS

CROSS REFERENCE TO RELATED APPLICATIONS

This application is a national stage application under 35 U.S.C. 371 and claims the benefit of PCT Application No. PCT/KR2012/007653 having an international filing date of 24 Sep. 2012, which designated the United States, which PCT application claimed the benefit of Korean Patent Application No. 10-2011-0096323 filed 23 Sep. 2011, the disclosures of which are incorporated herein by reference.

REFERENCE TO SEQUENCE LISTING

This application contains a Sequence Listing submitted as an electronic text file named "5624UIC-1_sequence_listing_ST25.txt", having a size in bytes of 3 KB, and created on Mar. 21, 2014. The information contained in this electronic file is hereby incorporated by reference in its entirety pursuant to 37 CFR §1.52(e)(5).

BACKGROUND OF THE INVENTION

1. Field of the Invention

The present invention relates to a pharmaceutical composition for preventing and treating endometriosis which comprises Puerariae Flos extract as an active ingredient, and a health food comprising the same.

2. Description of the Related Art

Endometriosis is a one of the most common gynecological diseases and its attack rate is about 3%~10% in childbearing age women and 25~35% in infertile women. This disease is characterized by abnormal proliferation of endometrial tissues in other organs such as ovary, abdominal cavity, digestive track, and urinary bladder than uterus and the implantation theory by Sampson has been accepted as the pathogenesis, which is that endometriosis is developed when endometrial tissues flow backward into abdominal cavity through fallopian tube and are implanted in ovary or peritoneum to grow. Symptoms of endometriosis are dysmenorrhoea, dyspareunia, and pains in other organs invaded (for example, Pneumothorax or hemothorax is observed when the endometrial tissue has invaded in the lung./Ureteral obstruction or hematuria is observed when the endometrial tissue has invaded in the ureter.). This disease can be a reason of infertility in 30~50% of total endometriosis patients. It has also been reported that endometriosis increases the risk of various cancers including ovarian cancer, renal cell carcinoma, and brain tumor.

Endometriosis cells are completely different from their origin, the normal endometrial cells, in their functions and in their molecular mechanism.

Endometriosis cells are estrogen-responsive but progesterone-unresponsive. Recent reports support the idea that endometriosis cells characterized by uncontrolled proliferation, anti-apoptosis, angiogenesis, migration and invasion, and change in local immune system are very similar to cancer cells in their characteristics (Farquhar, 2007; Fazleabas et al., 2004; Garai et al., 2006; Hastings and Fazleabas, 2003; Hastings and Fazleabas, 2006; Wu et al., 2007) (see FIG. 1). The most representative molecular biological characteristics of endometriosis are closely related to the over-expressions/over-productions of estrogen, prostaglandin, cytokine, and metalloproteinase (Bulun, 2009) (see FIG. 2).

The only and fundamental treatment for endometriosis so far is the surgical operation to eliminate the endometrium but this treatment has the disadvantage of high recurrence rate and might cause difficulty for a woman to have a baby later. For internal treatment for this disease, the conservative management using a pain killer or an anti-inflammatory agent, and the hormone therapy using danzol, progesterone, and gonadotropin-releasing hormone (GnRH) to regulate menstrual cycle have been used, but these are not fundamental treatment and only to alleviate symptoms or pains. Furthermore, the long-term treatment with those hormones causes other side effects (weight gain, fluid overload, fatigue, acne, oily skin, hirsutism, atropic vaginitis, hot flush, muscle spasm, anxiety, and hepatotoxicity). The recurrence rate is also as high as 70%. Endometriosis brings inconvenience in everyday life because of severe pain accompanied and is even a reason of infertility. Therefore, in the aspects of the 'quality of women's life' and 'pregnancy', this disease has to be considered as significant and as the one that has to be overcome. Nevertheless, a successful preventive and therapeutic method has not been established, yet, and studies on this matter are still in short. Thus, it is required to develop a preventive and therapeutic agent for endometriosis from natural substances that is more natural and thus has less side effects and outperforms the conventional methods such as surgical operation or simple pain management and menstrual cycle control, etc, in women particularly those in childbearing age.

Puerariae Flos is the flower of kudzu (Pueraria thunbergiana). According to the traditional medicine, this flower has been used to eliminate alcoholic poisoning or to relieve melena (Sanrim Gyeongje, Medicine, Puerariae radix). The leaf is also called Pueraria thunbergiana leaf that has been used to stop the bleeding of wound. The stem is called Pueraria thunbergiana stem that has been internally administered to treat laryngopharyngitis or applied externally to treat furuncle, for which Pueraria thunbergiana leaf is burn and powdered. The natural extract of Puerariae Flos long been administered according to the Oriental medicine has been targeted for the study of anti-inflammation and the result was presented in Journal of Ethnopharmacology in 2004 (J. Ethnopharmacol. 2004 September; 94(1):165-73.). The effect of the Puerariae Flos extract on the secretion of growth hormone has also been studied and published (Horm Metab Res. 2004 February; 36(2):86-91.). The effect of the Puerariae Flos and other Leguminosae plants originated materials on the activity of estrogen was also reported in 2005 (Biol Pharm Bull. 2005 March; 28(3):538-40.). According to another report (J Agric Food Chem. 2005 Jul. 27; 53(15):5882-8.), the Puerariae Flos extract could inhibit the reducing effect of beta-hydroxy-beta-methylglutaryl coenzyme A (HMG CoA), and this coenzyme inhibitor could further inhibit the synthesis of cholesterol, more precisely inhibit the synthesis of cholesterol in liver. In 2006, the result of a study saying that Daidzin originated from Puerariae Flos extract could activate choline acetyltransferase, the enzyme to synthesize the neurotransmitter, acetylcholine, bringing the effect of improving amnesia resulted from drug intoxication was reported (Biosci Biotechnol Biochem. 2006 January; 70(1):107-11.). In addition, kakkalide and tectoridin were identified as major components of Puerariae Flos extract (J Nat. Med. 2010 July; 64(3):313-20. Epub 2010 March 31.), and these kakkalide and tectoridin were confirmed to have estrogen effect by affecting estrogen receptor (ER) and estrogen related receptors (ERR1/2), according to the study with menopausal women (Biol Pharm Bull. 2006 June; 29(6):1202-6.).

The present inventors have studied how the extract of Puerariae Flos, the natural substance long been used in Oriental medicine, could affect endometriosis cells. As a result, the present inventors confirmed that the Puerariae Flos extract had the activity of inhibiting the migration of endometriosis cells, inhibiting the adhesion of the cells onto peritoneal cells, and inhibiting the expressions of the characteristic factors of endometriosis, by which the inventors completed this invention with presenting the Puerariae Flos extract as an active ingredient for a composition for preventing and treating endometriosis.

SUMMARY OF THE INVENTION

It is an object of the present invention to provide a pharmaceutical composition for preventing or treating endometriosis or the complications thereof which comprises Puerariae Flos extract as an active ingredient.

It is another object of the present invention to provide a health food composition for preventing or improving endometriosis or the complications thereof which comprises Puerariae Flos extract as an active ingredient.

It is also an object of the present invention to provide a method for preventing, improving, or treating endometriosis or the complications thereof which includes the step of administering Puerariae Flos extract to a subject.

It is further an object of the present invention to provide a use of Puerariae Flos extract for the preparation of a pharmaceutical composition or a health food for preventing, improving, or treating endometriosis or the complications thereof.

To achieve the above objects, the present invention provides a pharmaceutical composition for preventing or treating endometriosis or the complications thereof which comprises Puerariae Flos extract as an active ingredient.

The present invention also provides a health food composition for preventing or improving endometriosis or the complications thereof which comprises Puerariae Flos extract as an active ingredient.

The present invention also provides a method for treating endometriosis and the complications thereof which includes the step of administering a pharmaceutically effective dose of Puerariae Flos extract to a subject having endometriosis and the complications thereof.

The present invention further provides a method for preventing endometriosis and the complications thereof which includes the step of administering a pharmaceutically effective dose of Puerariae Flos extract to a subject.

The present invention also provides Puerariae Flos extract for the preparation of a pharmaceutical composition for preventing and treating endometriosis and the complications thereof.

The present invention also provides Puerariae Flos extract for the preparation of a health food for preventing and improving endometriosis and the complications thereof.

The present invention also provides a use of a pharmaceutically effective dose of Puerariae Flos extract for the preparation of a pharmaceutical composition for preventing and treating endometriosis and the complications thereof.

In addition, the present invention provides a use of a pharmaceutically effective dose of Puerariae Flos extract for the preparation of a health food for preventing and improving endometriosis and the complications thereof.

Advantageous Effect

As explained hereinbefore, the Puerariae Flos extract of the present invention has the activities of inhibiting the migration and adhesion of endometriosis cells, inhibiting the expressions of MMP-2 and MMP-9, which are factors associated with migration and adhesion, inhibiting the expression of COX-2, which is a factor associated with pain, and inhibiting the expressions of MCP-1, which is a cytokine associated with inflammation, and RANTES, so that the extract can be effectively used as an active ingredient of the pharmaceutical composition for preventing or treating endometriosis and the complications thereof and for the health food as well.

BRIEF DESCRIPTION OF THE DRAWINGS

The application of the preferred embodiments of the present invention is best understood with reference to the accompanying drawings, wherein.

DESCRIPTION OF THE PREFERRED EMBODIMENTS

Figure 1:
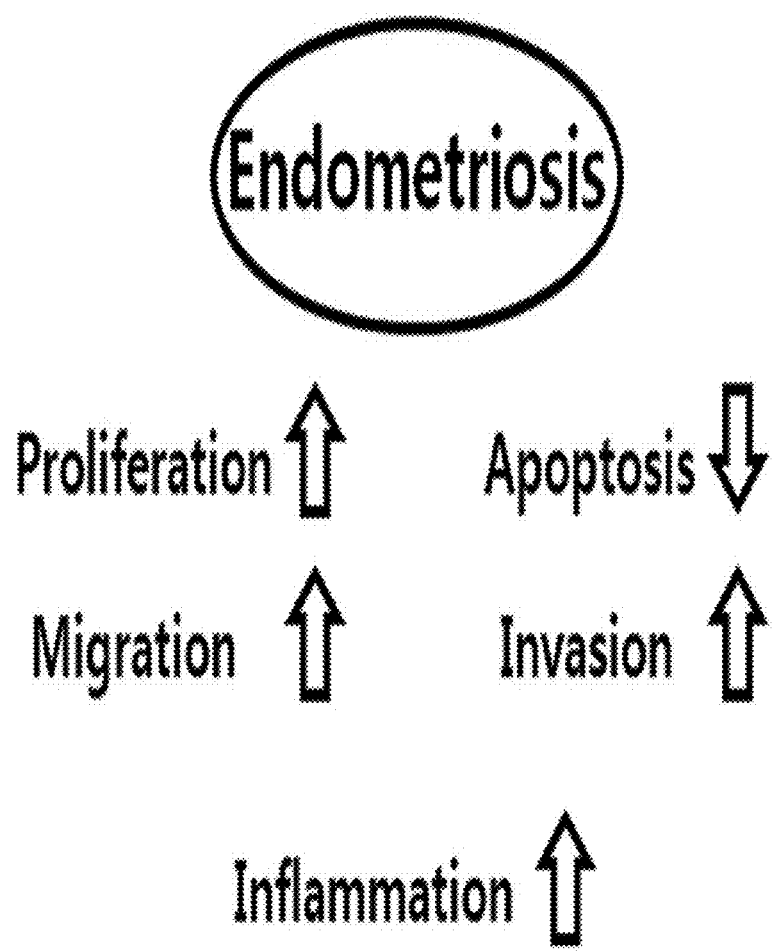
FIG. 1 is a diagram illustrating the characteristics of endometriosis cells.
Figure 2:
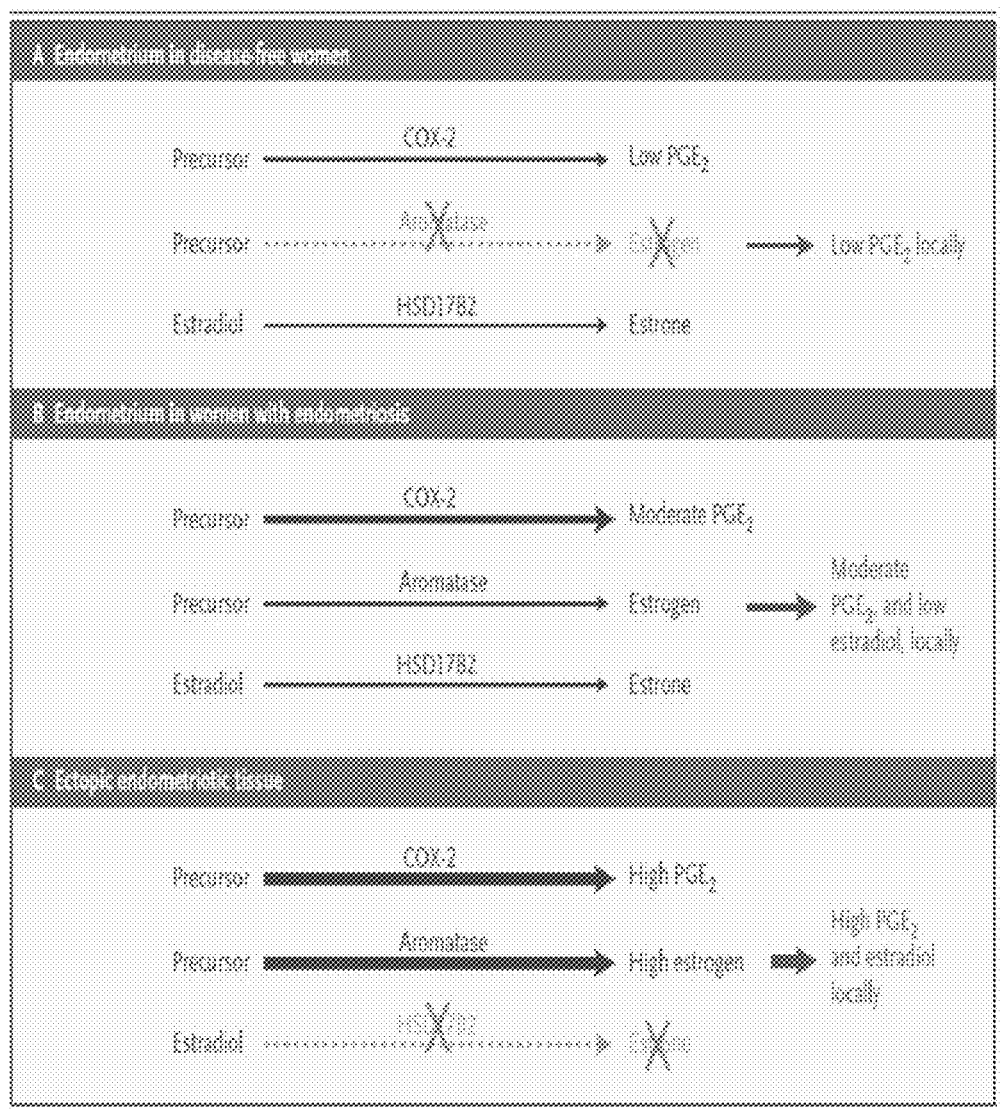
FIG. 2 is a diagram illustrating the difference among normal endometrium, endometriosis endometrium, and endometriosis tissue cells at molecular level.

Hereinafter, the present invention is described in detail.

The present invention provides a pharmaceutical composition for preventing or treating endometriosis or the complications thereof which comprises Puerariae Flos extract as an active ingredient.

The said endometriosis and the complications thereof herein are preferably presumed to be attributed to the over-expression of MMP-2, MMP-9, COX-2, MCP-1 or RANTES, but not always limited thereto.

The said complications of endometriosis herein is selected from the group consisting of pelvic inflammatory disease, pelvic adhesion, ovarian cystic tumor, myoma uteri, ectopic pregnancy, and infertility, but not always limited thereto.

The Puerariae Flos extract, the active ingredient of the present invention, is preferably prepared by the method comprising the following steps, but not always limited thereto:

1) selecting Puerariae Flos by sorting the plant material according to the parts;
2) drying the selected Puerariae Flos;
3) pulverizing the dried Puerariae Flos;
4) extracting the Puerariae Flos after adding an extraction solvent thereto;
5) filtering the extract obtained in step 4); and
6) freeze-drying the filtered extract of step 5). The Puerariae Flos herein can be either purchased or cultivated.

In the above method, the drying process of step 2) is preferably performed at room temperature in the shade for 1-10 days, and more preferably for 5 days, but not always limited thereto.

In the above method, the extraction solvent of step 4) is water, alcohol, or the mixture thereof, and more preferably $C_1$~$C_2$ lower alcohol or the mixed solvent thereof, but not always limited thereto. The lower alcohol is preferably ethanol or methanol, but not always limited thereto. The volume of the extraction solvent is preferably 5~15 times the dry weight of Puerariae Flos, and more preferably 10 times the dry weight, but not always limited thereto.

In the above method, the extraction method is preferably selected from the group consisting of hot-water extraction, soaking extraction, reflux cold extraction, ultrasonification extraction, and traditional extraction using a decoction vessel, but not always limited thereto. The extraction temperature is preferably 10° C.~100° C., and more preferably room temperature, but not always limited thereto. The extraction time is preferably 10 minutes~3 hours, and more preferably 15 minutes, but not always limited thereto. The extraction times are preferably 5~10 times a day, and more preferably 10 times a day. The extraction is preferably repeated for 3 days, but not always limited thereto.

In the above method, the drying process of step 6) is preferably performed by low pressure drying, vacuum drying, boiling drying, spray drying, or freeze drying, but not always limited thereto.

In a preferred embodiment of the present invention, the effect of Puerariae Flos extract on endometriosis was investigated. Particularly, Puerariae Flos extract was treated to the endometriosis cell lines 11Z and 12Z established from women having endometriosis, and then wound healing test and trans-well migration assay were performed to investigate the migration of endometriosis cells. As a result, the present inventors confirmed that Puerariae Flos extract inhibited the migration of endometriosis cells dose-dependently (see FIGS. 3~6).

In another preferred embodiment of the present invention, the present inventors investigated the effect of Puerariae Flos extract on the adhesion and implantation of endometriosis cells onto Met-5A cells covering the organs around the peritoneum and the abdominal cavity. As a result, it was confirmed that Puerariae Flos extract inhibited the adhesion of endometriosis cells thereto (see FIGS. 7 and 8).

In another preferred embodiment of the present invention, the present inventors also investigated whether or not Puerariae Flos extract could inhibit the expressions of MMP-2 and MMP-9, which are the factors associated with migration and adhesion and are over-expressed in endometriosis. Particularly, Puerariae Flos extract was treated to endometriosis cells, and then the expressions of endogenous MMP-2 and MMP-9 mRNA and proteins were measured. As a result, the expressions of MMP-2 and MMP-9, the factors associated with migration and adhesion, were significantly inhibited in the group treated with Puerariae Flos extract, compared with those of the control (see FIGS. 9~14).

In another preferred embodiment of the present invention, the present inventors investigated the effect of Puerariae Flos extract on the expression of COX-2 (cyclooxygenase-2), which is related to pain and inflammation caused by endometriosis. Particularly, Puerariae Flos extract was treated to endometriosis cells, and then the expression of COX-2 mRNA was measured. As a result, the expression of COX-2 was significantly reduced in the experimental group treated with Puerariae Flos extract, compared with that of the control (see FIG. 15).

In another preferred embodiment of the present invention, the inventors investigated the effect of Puerariae Flos extract on the expressions of MCP-1 known as a cytokine that is over-expressed in endometriosis cells, and RANTES. Particularly, Puerariae Flos extract was treated to endometriosis cells, and then the expressions of MCP-1 and RANTES mRNA were measured. As a result, the expressions of MCP-1 and RANTES mRNA were significantly reduced in the group treated with Puerariae Flos extract, compared with those of the control (see FIGS. 16 and 17).

From the above results, it was confirmed that the Puerariae Flos extract of the present invention had the activities of inhibiting the migration and adhesion of endometriosis cells, inhibiting the expressions of MMP-2 and MMP-9, the factors associated with migration and adhesion, inhibiting the expression of COX-2, the factor associated with pain, and inhibiting the expressions of MCP-1, the cytokine associated with inflammation, and RANTES. Therefore, the Puerariae Flos extract of the present invention was confirmed to be effectively used as an active ingredient for the pharmaceutical composition for preventing or treating endometriosis and the complications thereof.

The Puerariae Flos extract of the present invention can additionally include a pharmaceutically acceptable additive, which is exemplified by starch, gelatinized starch, microcrystalline cellulose, lactose, povidone, colloidal silicon dioxide, calcium hydrogen phosphate, lactose, mannitol, taffy, Arabia rubber, pregelatinized starch, corn starch, cellulose powder, hydroxypropyl cellulose, Opadry, sodium carboxy methyl starch, carunauba wax, synthetic aluminum silicate, stearic acid, magnesium stearate, aluminum stearate, calcium stearate, white sugar, dextrose, sorbitol, talc, etc. The pharmaceutically acceptable additive herein is preferably added by 0.1~90 weight part to the composition, but not always limited thereto.

That is, the composition of the present invention can be prepared for oral or parenteral administration by mixing with generally used diluents or excipients such as fillers, extenders, binders, wetting agents, disintegrating agents and surfactants. Solid formulations for oral administration are tablets, pills, powders, granules and capsules. These solid formulations are prepared by mixing the said Puerariae Flos extract with one or more suitable excipients such as starch, calcium carbonate, sucrose or lactose, gelatin, etc. Except for the simple excipients, lubricants, for example magnesium stearate, talc, etc, can be used. Liquid formulations for oral administrations are suspensions, solutions, emulsions and syrups, and the above-mentioned formulations can contain various excipients such as wetting agents, sweeteners, aromatics and preservatives in addition to generally used simple diluents such as water and liquid paraffin. Formulations for parenteral administration are sterilized aqueous solutions, water-insoluble excipients, suspensions, emulsions, lyophilized preparations and suppositories. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, tween 61, cacao butter, laurin butter, glycerogelatin, etc.

The composition of the present invention can be administered orally or parenterally, and the parenteral administration includes skin external application, intraperitoneal injection, intrarectal injection, subcutaneous injection, intravenous injection, intramuscular injection, and intrathoracic injection. The effective dose of the composition can be determined according to weight, age, gender, health condition, diet, administration frequency, administration method, excretion and severity of disease.

The effective dose of the composition of the present invention can be determined according to weight, age, gender, health condition, diet, administration frequency, administration method, excretion and severity of disease. The dose of Puerariae Flos extract is 0.0001~100 mg/kg per day and preferably 0.001~10 mg/kg per day, and administration frequency is preferably 1~6 times a day.

The present invention also provides a method for preventing or treating endometriosis and the complications thereof which includes the step of administering a pharmaceutically effective dose of Puerariae Flos extract to a subject.

The pharmaceutically effective dose herein is 0.0001-100 mg/kg per day and preferably 0.001-10 mg/kg per day, but not always limited thereto. The effective dose can be determined according to weight, age, gender, health condition, diet, administration frequency, administration method, excretion and severity of disease.

The said subject is a vertebrate, preferably a mammal, more preferably a test animal such as rat, rabbit, guinea pig, hamster, dog and cat, and most preferably an anthropoid such as chimpanzee and gorilla.

The Puerariae Flos extract of the present invention can be administered orally or parenterally, and the parenteral administration includes intraperitoneal injection, intrarectal injection, subcutaneous injection, intravenous injection, intramuscular injection, intrauterine injection, and intracerebroventricular injection.

The present invention also provides a method for preventing recurrence of endometriosis which includes the step of administering a pharmaceutically effective dose of Puerariae Flos extract to a subject who had endometriosis once.

The pharmaceutically effective dose herein is 0.0001-100 mg/kg per day and preferably 0.001-10 mg/kg per day, but not always limited thereto. The effective dose can be determined according to weight, age, gender, health condition, diet, administration frequency, administration method, excretion and severity of disease.

The said subject is a vertebrate, preferably a mammal, more preferably a test animal such as rat, rabbit, guinea pig, hamster, dog and cat, and most preferably an anthropoid such as chimpanzee and gorilla.

The Puerariae Flos extract of the present invention can be administered orally or parenterally, and the parenteral administration includes intraperitoneal injection, intrarectal injection, subcutaneous injection, intravenous injection, intramuscular injection, intrauterine injection, and intracerebroventricular injection.

The present invention also provides a health food composition for preventing or improving endometriosis or the complications thereof which comprises the Puerariae Flos extract prepared by the above method as an active ingredient.

The said endometriosis and the complications thereof herein are preferably presumed to be attributed to the over-expression of MMP-2, MMP-9, COX-2, MCP-1 or RANTES, but not always limited thereto.

The said complications of endometriosis herein is selected from the group consisting of pelvic inflammatory disease, pelvic adhesion, ovarian cystic tumor, myoma uteri, ectopic pregnancy, and infertility, but not always limited thereto.

In preferred embodiments of the present invention, the present inventors confirmed that the Puerariae Flos extract of the present invention had the activities of inhibiting the migration and adhesion of endometriosis cells, inhibiting the expressions of MMP-2 and MMP-9, the factors associated with migration and adhesion, inhibiting the expression of COX-2 (cyclooxygenase-2), the factor associated with pain, and inhibiting the expressions of MCP-1, the cytokine associated with inflammation, and RANTES.

Therefore, the Puerariae Flos extract of the present invention was confirmed to be effectively used as an active ingredient for the health food composition for preventing or improving endometriosis and the complications thereof.

The Puerariae Flos extract of the present invention can be used as a food additive. In that case, the Puerariae Flos extract of the present invention can be added as it is or as mixed with other food components according to the conventional method.

The health food herein is not limited. For example, the Puerariae Flos extract of the present invention can be added to meats, sausages, breads, chocolates, candies, snacks, cookies, pizza, ramyuns, flour products, gums, dairy products including ice cream, soups, beverages, tea, drinks, alcohol drinks and vitamin complex, etc, and in wide sense, almost every food applicable in the production of health food can be included.

The composition for health beverages of the present invention can additionally include various flavors or natural carbohydrates, etc, like other beverages. The natural carbohydrates above can be one of monosaccharides such as glucose and fructose, disaccharides such as maltose and sucrose, polysaccharides such as dextrin and cyclodextrin, and glucose alcohols such as xilytole, sorbitol and erythritol. Besides, natural sweetening agents such as thaumatin and stevia extract, and synthetic sweetening agents such as saccharin and aspartame can be included as a sweetening agent. The content of the natural carbohydrate is preferably 0.01-0.04 g and more preferably 0.02-0.03 g in 100 g of the composition of the present invention.

In addition to the ingredients mentioned above, the health food of the present invention can include in a variety of nutrients, vitamins, minerals, flavors, coloring agents, pectic acid and its salts, alginic acid and its salts, organic acid, protective colloidal viscosifiers, pH regulators, stabilizers, antiseptics, glycerin, alcohols, carbonators which used to be added to soda, etc. The health food of the present invention can also include natural fruit juice, fruit beverages and/or fruit flesh addable to vegetable beverages. All the mentioned ingredients can be added singly or together. The mixing ratio of those ingredients does not matter in fact, but in general, each can be added by 001-0.1 weight part per 100 weight part of the composition of the present invention.

The present invention also provides Puerariae Flos extract for the preparation of a pharmaceutical composition for preventing and treating endometriosis and the complications thereof.

The present invention also provides Puerariae Flos extract for the preparation of a health food for preventing and improving endometriosis and the complications thereof.

The present invention also provides a use of a pharmaceutically effective dose of Puerariae Flos extract for the preparation of a pharmaceutical composition for preventing and treating endometriosis and the complications thereof.

In addition, the present invention provides a use of a pharmaceutically effective dose of Puerariae Flos extract for the preparation of a health food for preventing and improving endometriosis and the complications thereof.

The said endometriosis and the complications thereof herein are preferably presumed to be attributed to the over-expression of MMP-2, MMP-9, COX-2, MCP-1 or RANTES, but not always limited thereto.

The said complications of endometriosis herein is selected from the group consisting of pelvic inflammatory disease, pelvic adhesion, ovarian cystic tumor, myoma uteri, ectopic pregnancy, and infertility, but not always limited thereto.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Preparation of Puerariae Flos Extract

The present inventors purchased Puerariae Flos extract prepared by extraction using a traditional decoction vessel from Plant Extract Bank, Korea Research Institute of Bioscience and Biotechnology.

Particularly, to prepare Puerariae Flos extract in Plant Extract Bank, the plant material was sorted by the parts and the selected Puerariae Flos was dried at room temperature in the shade for about 5 days, followed by pulverization. The pulverized Puerariae Flos sample was mixed with deionized water at the ratio of 1:10. The mixture was loaded in a decoction vessel, followed by hot-water extraction for 3 hours. Then, the solution was filtered. The moisture was eliminated by using a freeze dryer to give the extract.

Experimental Example 1

Inhibition of Endometriosis Cell Migration by Puerariae Flos Extract

<1-1> Inhibitory Effect of Puerariae Flos Extract on Wound Healing

Wound healing assay was performed to investigate the effect of Puerariae Flos extract on the migration of endometriosis cells.

Particularly, to examine the cell migration, the human immortalized endometriosis cell lines 11Z (Johann-Wolfgang-Goethe-Universitaet, Germany) and 12Z (Johann-Wolfgang-Goethe-Universitaet, Germany), established from active endometriotic lesion, were cultured in DMEM/F12 medium supplemented with 10% FBS, 100 U/ml penicillin G and 100 g/ml streptomycin (Life Technologies, Grand Island, N.Y.) in a 37° C. 5% $CO_2$ incubator. The said 11Z and 12Z cells were distributed in each well of 12-well plate at the density of $5 \times 10^5$ cells/well. The cells were cultured in DMEM/F12 medium (Life Technologies, Grand Island, N.Y.) at 37° C. until the confluency reached 80-90%. Then, the medium was discarded and the denuded zone (gap) in a regular width was made by scratching the middle of monolayer with a micro pipette tip. Cell debris were washed with PBS and then the cells were exposed on Puerariae Flos extract (25 ug/ml, 50 ug/ml and 100 ug/ml). The photograph of early cell monolayer showing the spot of wound underlined was compared with the photographs of cell monolayers cultured for 0, 2, 8, and 24 hours. As a result, the cells were migrated enough to fill the wound and the number of cells migrated over the line marking the original wound was counted in 6 random fields of each triplicate, which was presented in a graph.

Figure 3:
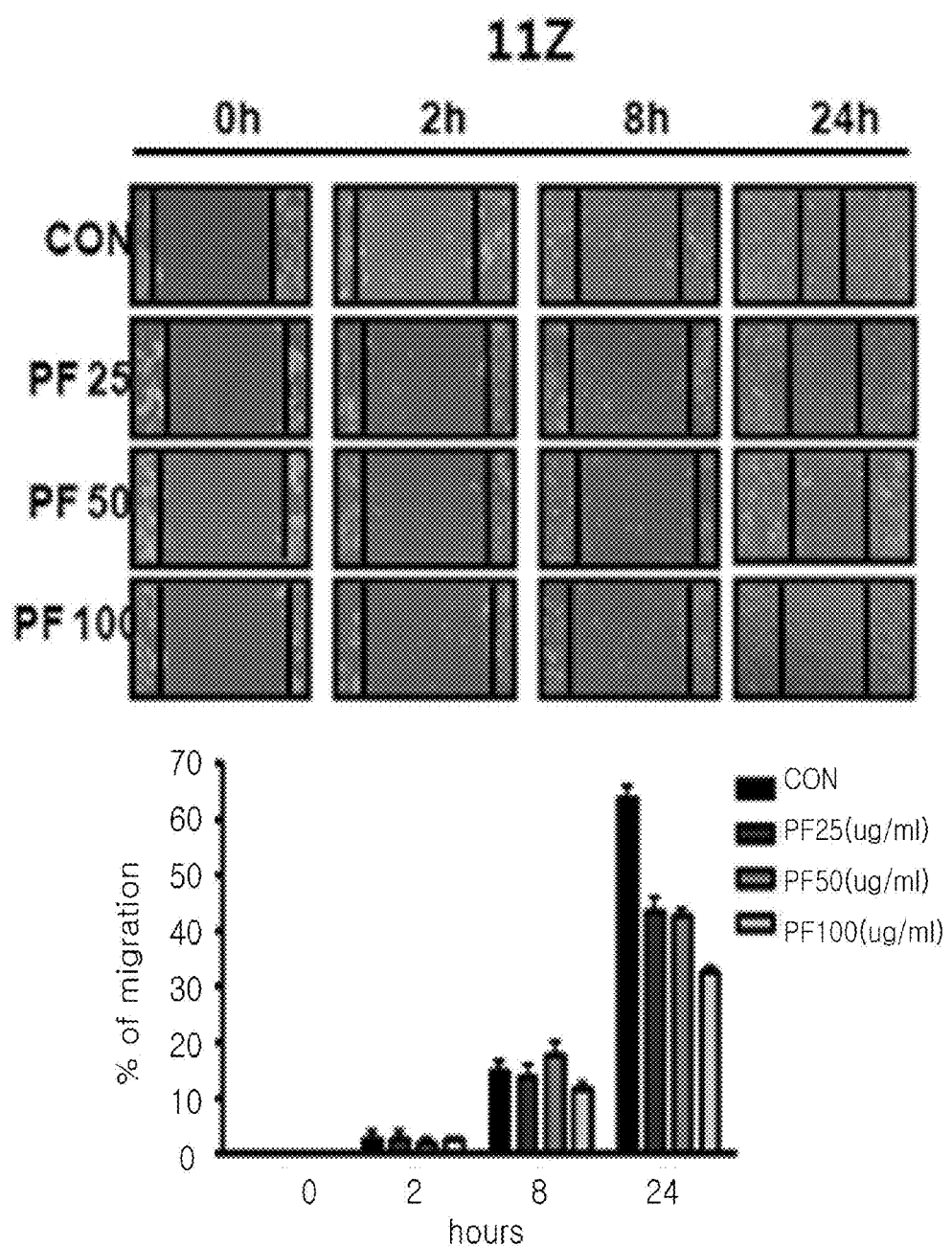
FIG. 3 is a diagram illustrating the migration of the endometriosis cell line 11Z, confirmed by wound healing assay;
CON: control;
PF 25: the group treated with 25 ug/ml of Puerariae Flos extract (PF);
PF 50: the group treated with 50 ug/ml of Puerariae Flos extract (PF); and PF 100: the group treated with 100 ug/ml of Puerariae Flos extract (PF).
Figure 4:
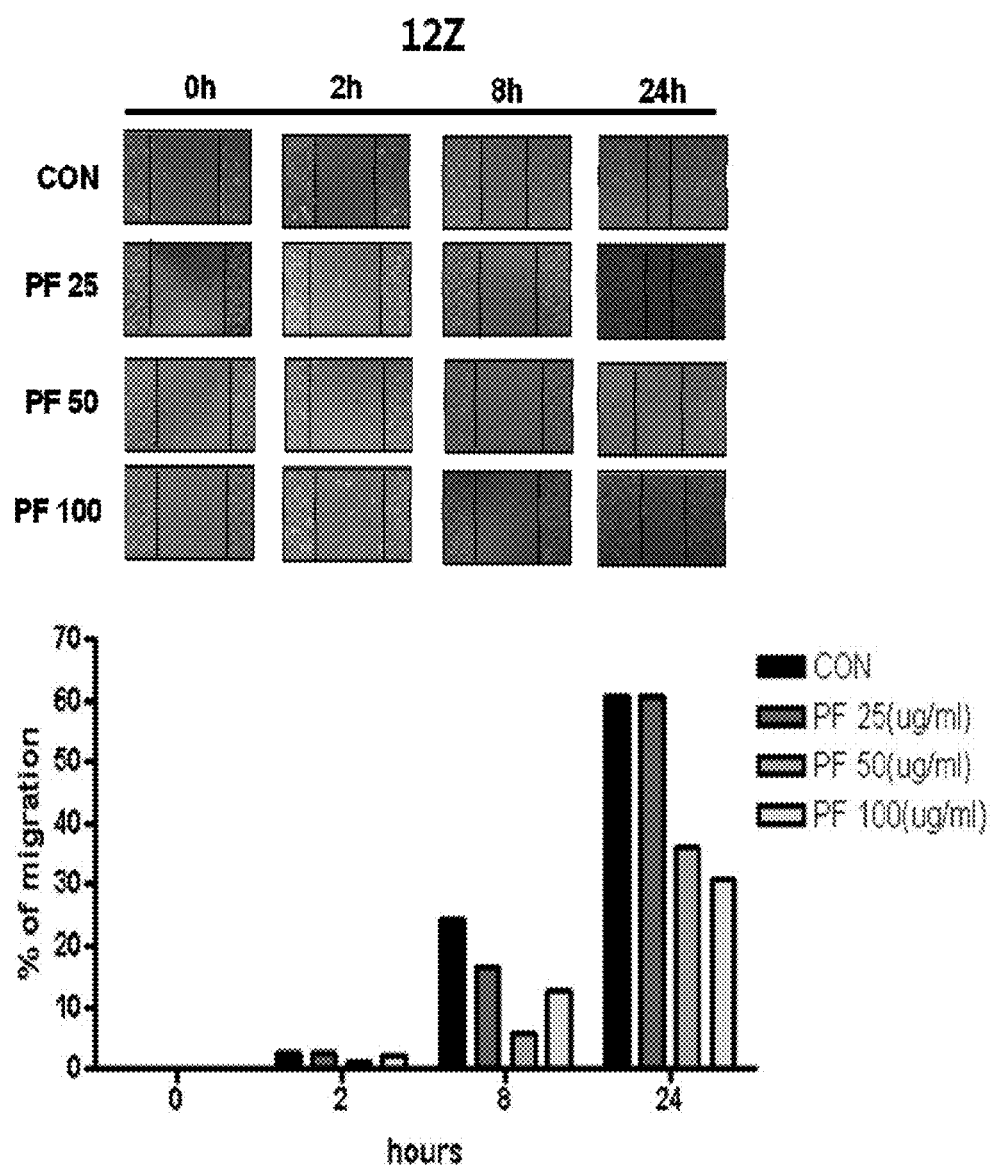
FIG. 4 is a diagram illustrating the migration of the endometriosis cell line 12Z, confirmed by wound healing assay;
CON: control;
PF 25: the group treated with 25 ug/ml of Puerariae Flos extract (PF);
PF 50: the group treated with 50 ug/ml of Puerariae Flos extract (PF); and PF 100: the group treated with 100 ug/ml of Puerariae Flos extract (PF).

From the above results, it was confirmed that the wound healing of 11Z and 12Z, the endometriosis cells treated with Puerariae Flos extract, were retarded dose-dependently, indicating that the Puerariae Flos extract of the present invention inhibited the migration of endometriosis cells (FIG. 3 and FIG. 4).

<1-2> Inhibition of Endometriosis Cell Migration by Puerariae Flos Extract

To investigate whether or not the Puerariae Flos extract of the present invention could affect endometriosis cell migration, transwell-migraion assay was performed in triplicate.

Particularly, the endometriosis cell lines 11Z and 12Z were distributed in the upper part of each trans-well of 24 well-transwell plate (8 um pore size), which was treated with Puerariae Flos extract at the concentrations of 25 ug/ml, 50 ug/ml, and 100 ug/ml. 8 hour or 24 hours after the treatment with Puerariae Flos extract, the cells migrated to the outer wall of the trans-well were fixed with methanol, followed by staining with 0.5% crystal violet for 10 minutes. The cells migrated to the outer wall of the trans-well were counted under 200× microscope, which was presented in the graph.

Figure 5:
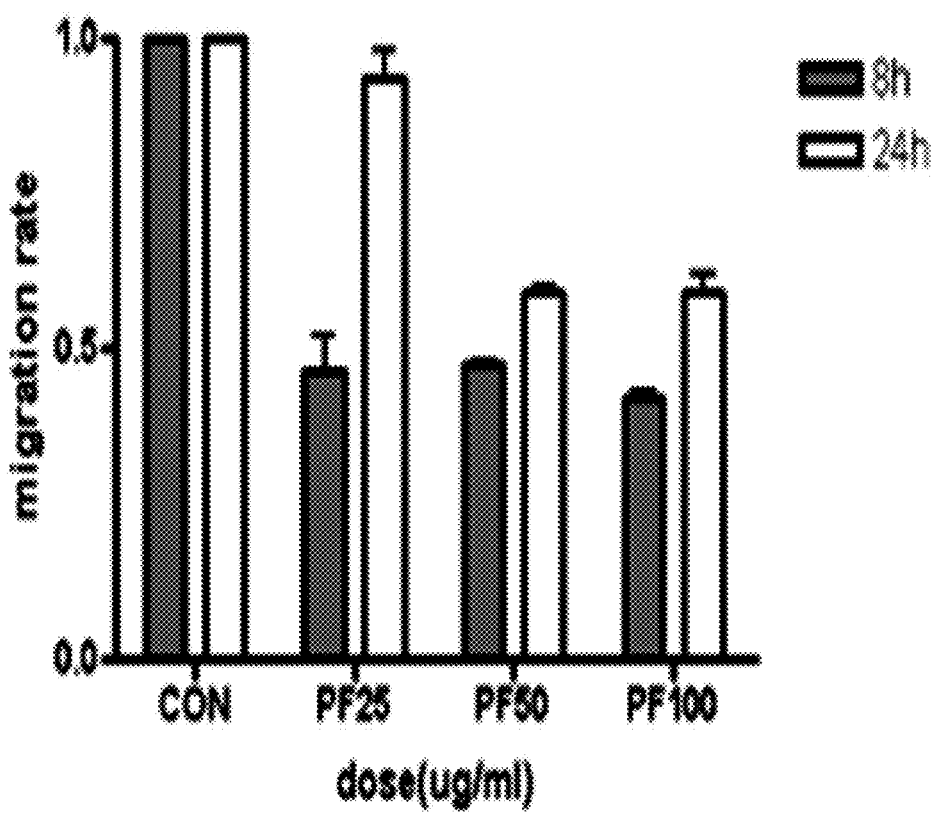
FIG. 5 is a diagram illustrating the migration of the endometriosis cell line 11Z;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).
Figure 6:
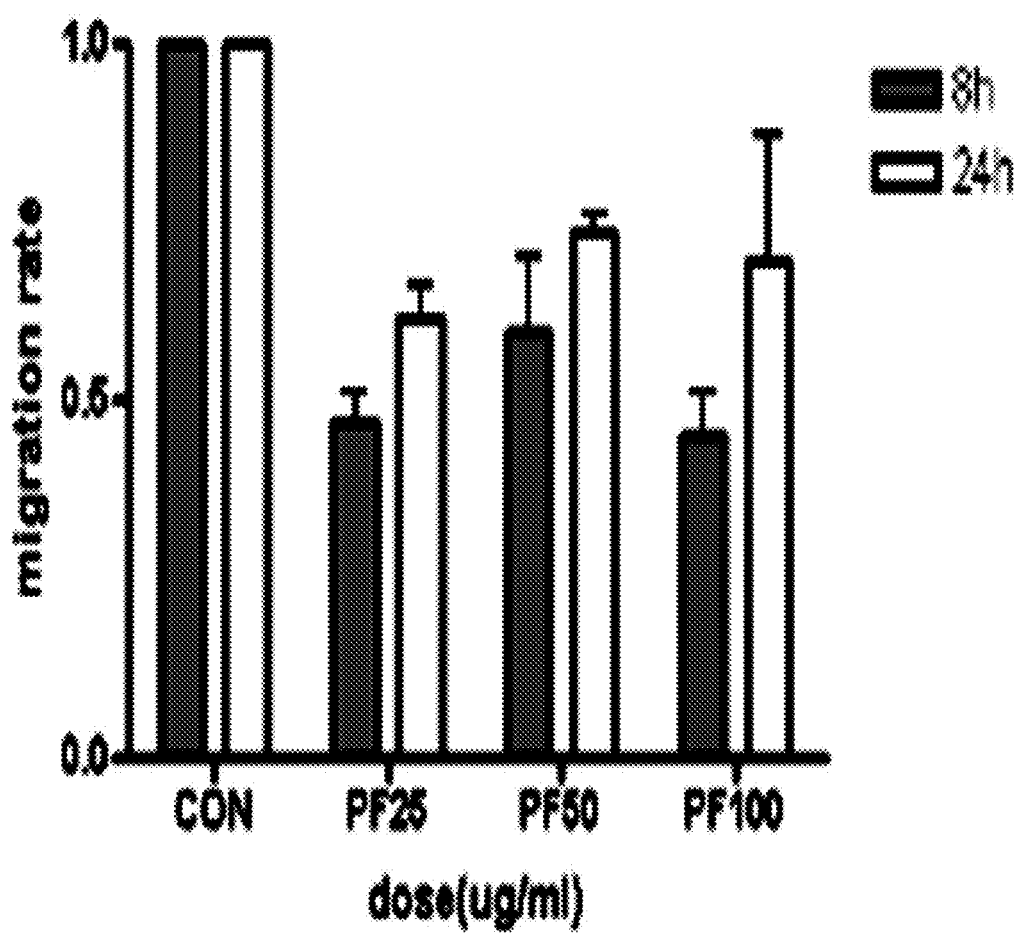
FIG. 6 is a diagram illustrating the migration of the endometriosis cell line 12Z;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).

As a result, it was confirmed that the migration of 11Z and 12Z, the endometriosis cells treated with Puerariae Flos extract for 8 or 24 hours, was significantly inhibited (FIG. 5 and FIG. 6).

Experimental Example 2

Inhibition of Endometriosis Cell Adhesion and Implantation by Puerariae Flos Extract To investigate whether or not the Puerariae Flos extract of the present invention could affect endometriosis cell adhesion and implantation, attachment assay was performed in triplicate.

Particularly, to investigate whether or not Puerariae Flos extract could inhibit the adhesion and implantation of endometriosis cells onto other organs around the peritoneum and abdominal cavity, which are characteristically shown in endometriosis, Met-5A cells (American Type Culture Collection, ATCC), the human peritoneal methothelial cells, were cultured in 199 medium supplemented with 10% FBS, 100 u/ml penicillin G, 100 g/ml streptomycin (Life Technologies, Grand Island, N.Y., U.S.A.), and 400 nM hydrocortisone (Sigma Chemical Co, St. Louis, Mo., U.S.A.) in a 5% $CO_2$ incubator. The Met-5A cells were distributed in a 96-well plate. The endometriosis cell lines 11Z and 12Z labeled with cell tracker green CMFDA ($2 \times 10^3$ cells/well) were mixed with DMEM/F12 medium supplemented with Puerariae Flos extract at the concentration of 25 ug/ml, 50 ug/ml, or 100 ug/ml. The mixture was added to the Met-5A cells distributed earlier. The mixed cells were cultured in a 37° C. 5% $CO_2$ incubator for 1 hour. The plate was turned down and washed with phosphate-buffered solution containing calcium and magnesium. The adhered cells were analyzed at $490_{nm}$ and the result was presented as % by the control (set as 100%).

Figure 7:
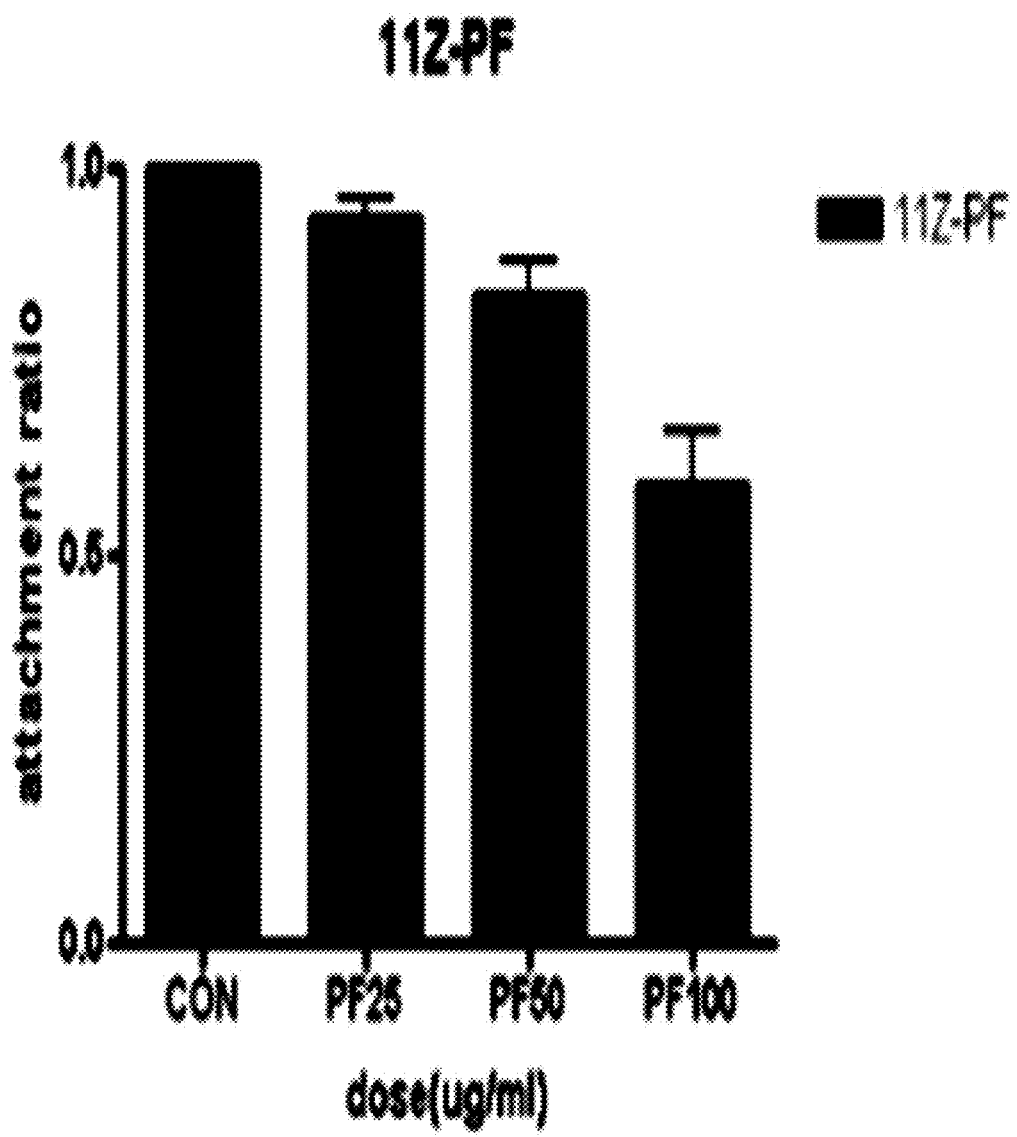
FIG. 7 is a diagram illustrating the adhesion of the endometriosis cell line 11Z onto the peritoneal mesothelium;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).
Figure 8:
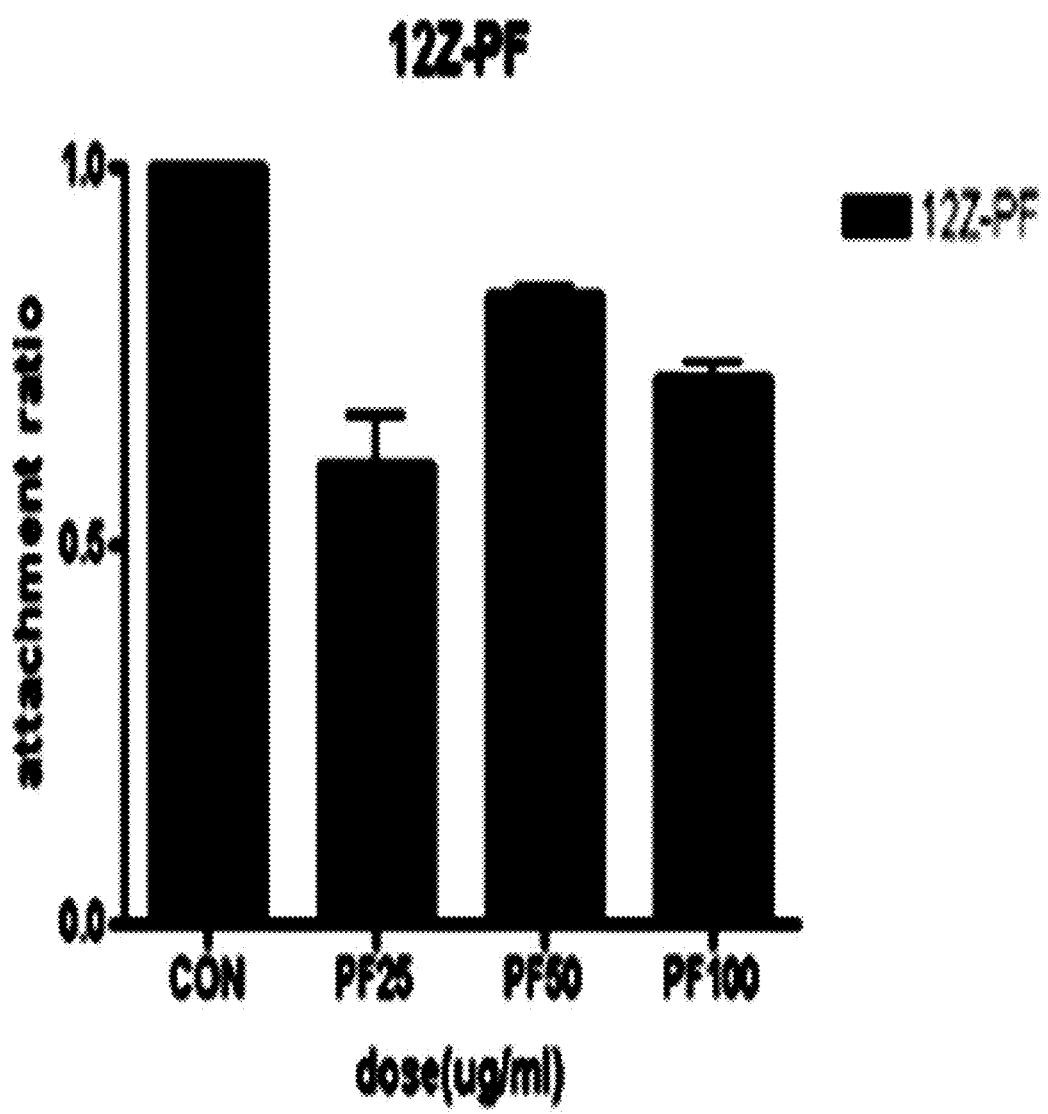
FIG. 8 is a diagram illustrating the adhesion of the endometriosis cell line 12Z onto the peritoneal mesothelium;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).

As a result, it was confirmed that the Puerariae Flos extract of the present invention significantly inhibited the adhesion of the endometriosis cell lines 11Z and 12Z on Met-5A cells covering the organs around the peritoneum and the abdominal cavity (FIG. 7 and FIG. 8).

Experimental Example 3

Inhibition of Endometriosis Cell Migration and Adhesion by Puerariae Flos Extract <3-1> Inhibitory Effect of Puerariae Flos Extract on the Expressions of MMP-2 and MMP-9 mRNA To investigate whether or not the Puerariae Flos extract of the present invention could inhibit the expressions of MMP-2 and MMP-9 mRNA, the proteases playing an important role in migration and invasion of endometriosis cells, real-time PCR was performed.

Particularly, the endometriosis cell lines 11Z and 12Z were treated with Puerariae Flos extract at the concentration of 25 ug/ml, 50 ug/ml, or 100 ug/ml for 24 hours. Total RNA was extracted from the 11Z and 12Z by the conventional method using TRIzol (Invitrogen Canada, Burlington, ON, Canada) known to those in the art. Reverse transcription polymerase chain reaction (RT-PCR) was performed with the total RNA to obtain the first-strand cDNA. Then, SYBR Green real-time PCR was performed using the first-strand cDNA amplified by PCR as a template with Thermal Cycler Dice Real Time PCR System (Takara, Japan) as follows; denaturation at 95° C. for 5 seconds, annealing at 57° C. for 10 seconds, extension at 72° C. for 20 seconds, 45 cycles from denaturation to extension. MMP-2 primers, MMP-9 primers, and the control GAPDH primers used in the said SYBR Green real-time PCR are as shown in [Table 1]. The average Ct values of MMP-2 and MMP-9 were obtained in triplicate and modified by Ct value of the control GAPDH.

TABLE 1

| | | | |
|---|---|---|---|
| MMP-2 sense primer | 5'- | ACCGCGACAAGAAGTATGGC- 3' | SEQ. ID. NO: 1 |
| antisense primer | 5'- | CCACTTGCGGTCATCATCGT- 3' | SEQ. ID. NO: 2 |
| MMP-9 sense primer | 5'- | CGATGACGAGTTGTGGTCCC- 3' | SEQ. ID. NO: 3 |
| antisense primer | 5'- | TCGTAGTTGGCCGTGGTACT- 3' | SEQ. ID. NO: 4 |
| GAPDH sense primer | 5'- | GAGTCAACGGATTTGGTCGT- 3 | SEQ. ID. NO: 5 |
| antisense primer | 5'- | TTGATTTTGGAGGGATCTCG- 3' | SEQ. ID. NO: 6 |

Figure 9:
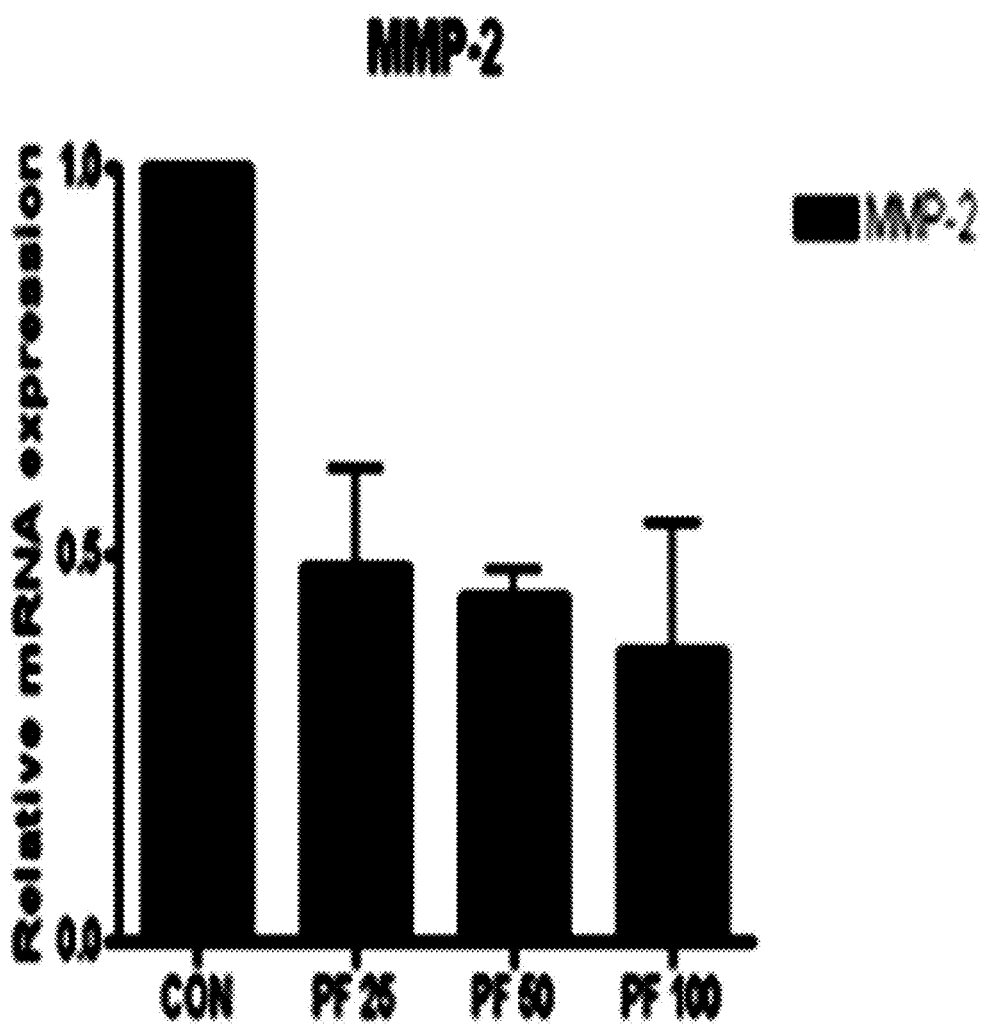
FIG. 9 is a diagram illustrating the expression of MMP-2 mRNA in the endometriosis cell line 11Z;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).
Figure 10:
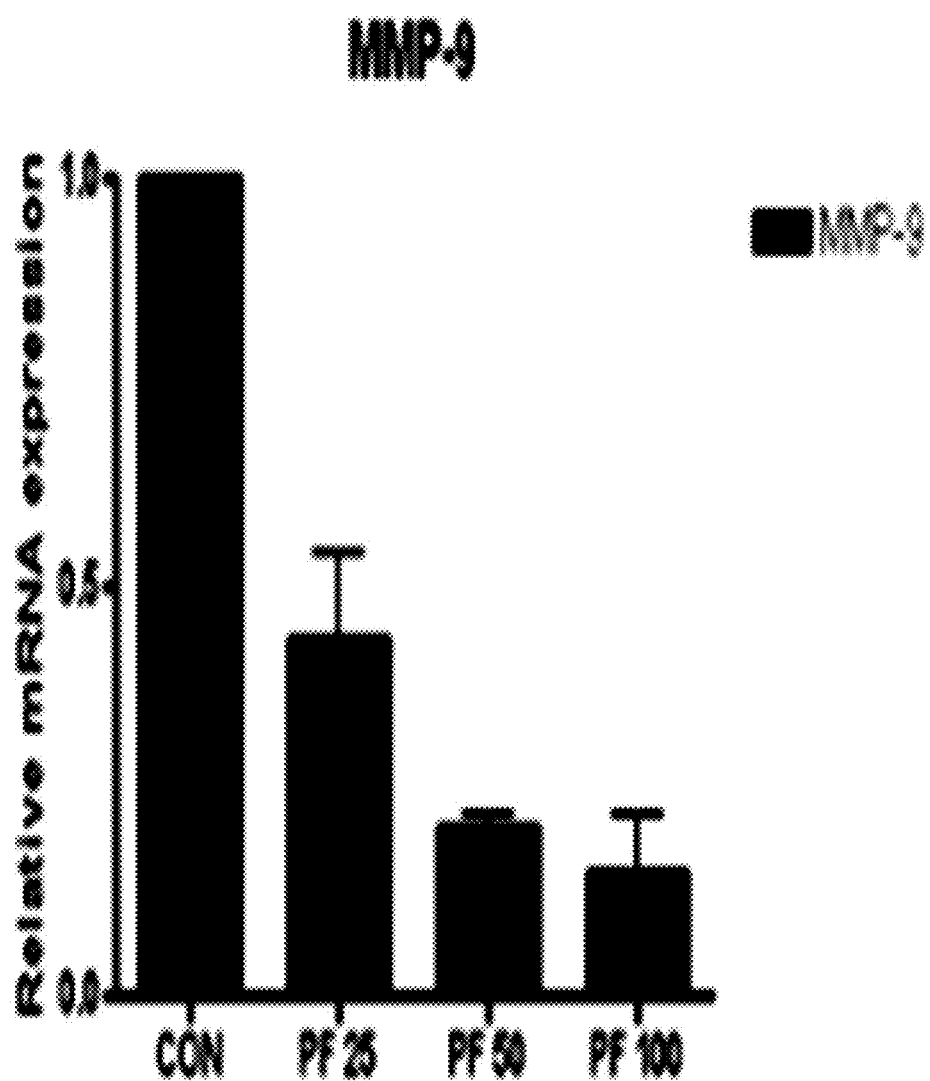
FIG. 10 is a diagram illustrating the expression of MMP-9 mRNA in the endometriosis cell line 11Z;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).
Figure 11:
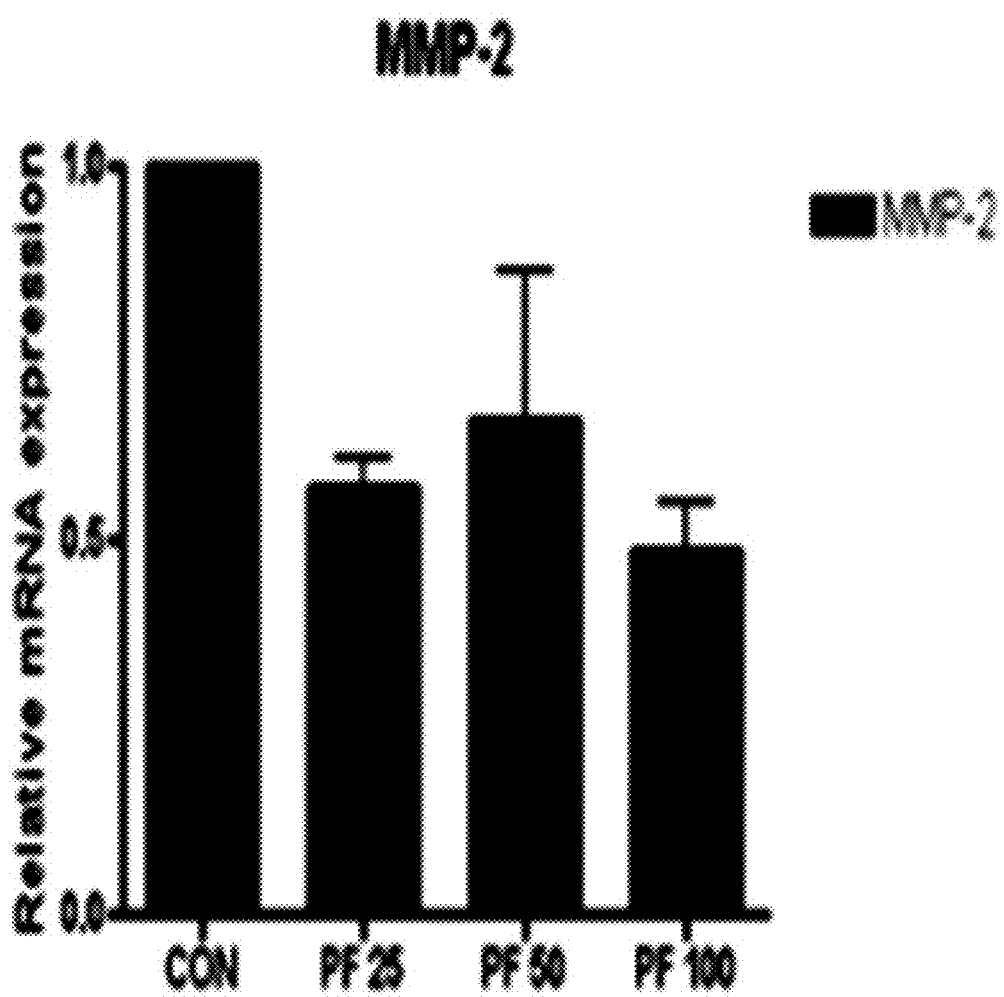
FIG. 11 is a diagram illustrating the expression of MMP-2 mRNA in the endometriosis cell line 12Z;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).
Figure 12:
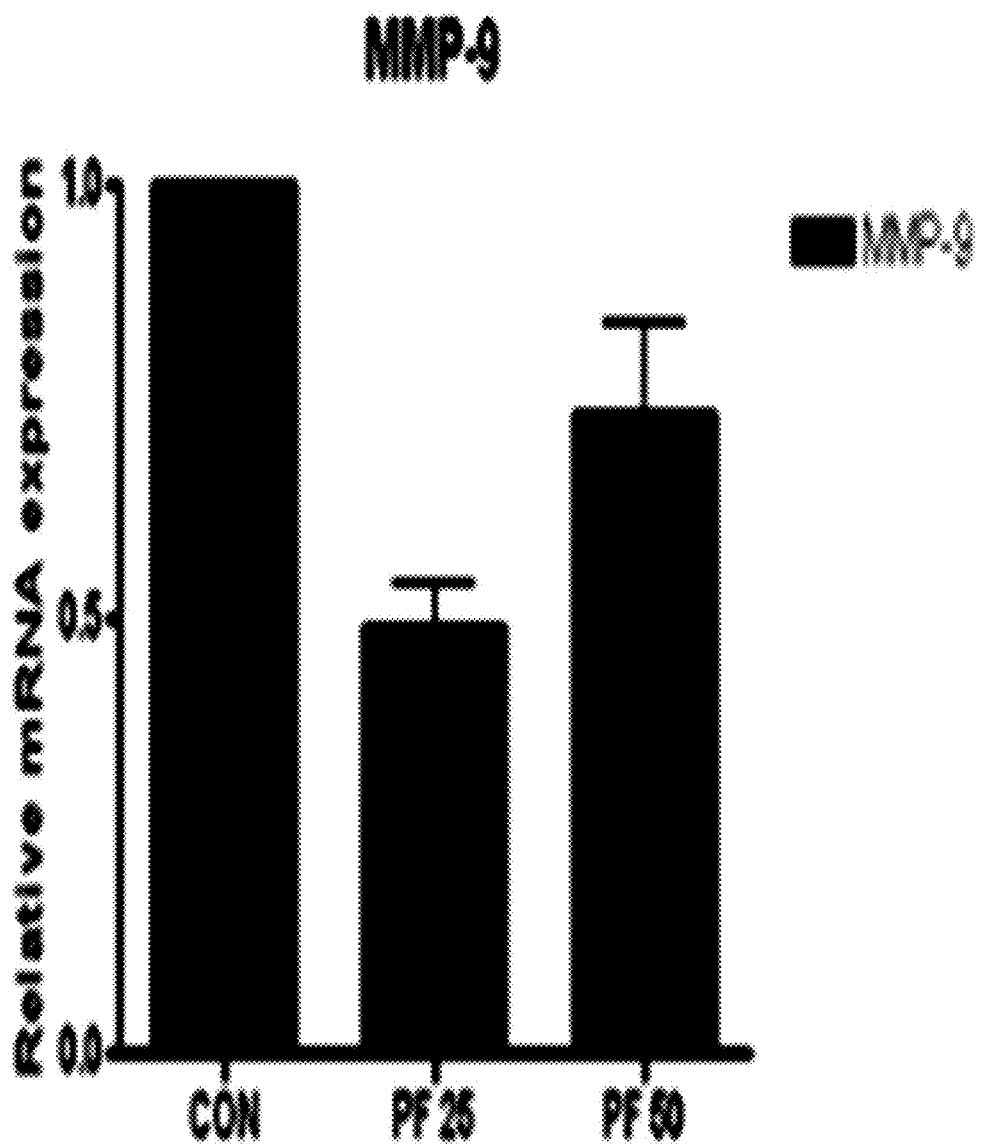
FIG. 12 is a diagram illustrating the expression of MMP-9 mRNA in the endometriosis cell line 12Z;
CON: control;
PF 25: the group treated with 25 ug/ml of Puerariae Flos extract (PF);
PF 50: the group treated with 50 ug/ml of Puerariae Flos extract (PF); and
PF 100: the group treated with 100 ug/ml of Puerariae Flos extract (PF).

As a result, it was confirmed in the endometriosis cell lines 11Z and 12Z that the mRNA expressions of MMP-2 and MMP-9, which are the representative proteins expressed in endometriosis and play an important role in cell migration and invasion, were significantly inhibited by Puerariae Flos extract (FIG. 9 and FIG. 10).

<3-2> Inhibitory Effect of Puerariae Flos Extract on the Expressions of MMP-2 and MMP-9 Protein To investigate whether or not the Puerariae Flos extract of the present invention could inhibit the expressions of MMP-2 and MMP-9 proteins, the proteases playing an important role in migration and invasion of endometriosis cells, Western blotting was performed.

Particularly, the endometriosis cell lines 11Z and 12Z were treated with Puerariae Flos extract at the concentration of 25 ug/ml, 50 ug/ml, or 100 ug/ml for 24 hours. The cells were then lysed in lysis buffer (Intron, Seoul, Korea), followed by quantification of the protein by Bradford assay and modification thereafter. The protein sample obtained from the cell lysate was mixed with the equal amount of 5×SDS sample buffer, which was heated for 4 minutes, followed by centrifugation with 10%~12% SDS-PAGE gel. The protein on the gel was transferred onto PVDF (polyvinylidene difluoride) membrane. The membrane was blocked by using 2.5% skim milk for 30 minutes, followed by washing. The membrane was reacted at 4° C. overnight in TBS-T solution (Tris-buffered saline containing 0.1% Tween-20) containing the primary antibodies anti-MMP-2 (Cell Signaling Technology, USA), anti-MMP-9 (Santa Cruz Biotechnology, CA, USA), and the control anti-beta-actin (Santa Cruz Biotechnology, CA, USA). Then, the primary antibodies were removed by washing the membrane with TBS-T solution three times. The membrane was reacted with the HRP (horseradish peroxidase)-conjugated secondary antibody (Santa Cruz Biotechnology, CA, USA) diluted at the ratio of 1:1000~1:2000 for 1 hour. The membrane reacted with the secondary antibody was washed with TBS-T solution three times, followed by chemiluminescence. Then, the membrane was analyzed with ImageQuant Las-4000 (Tokyo, Japan).

Figure 13:
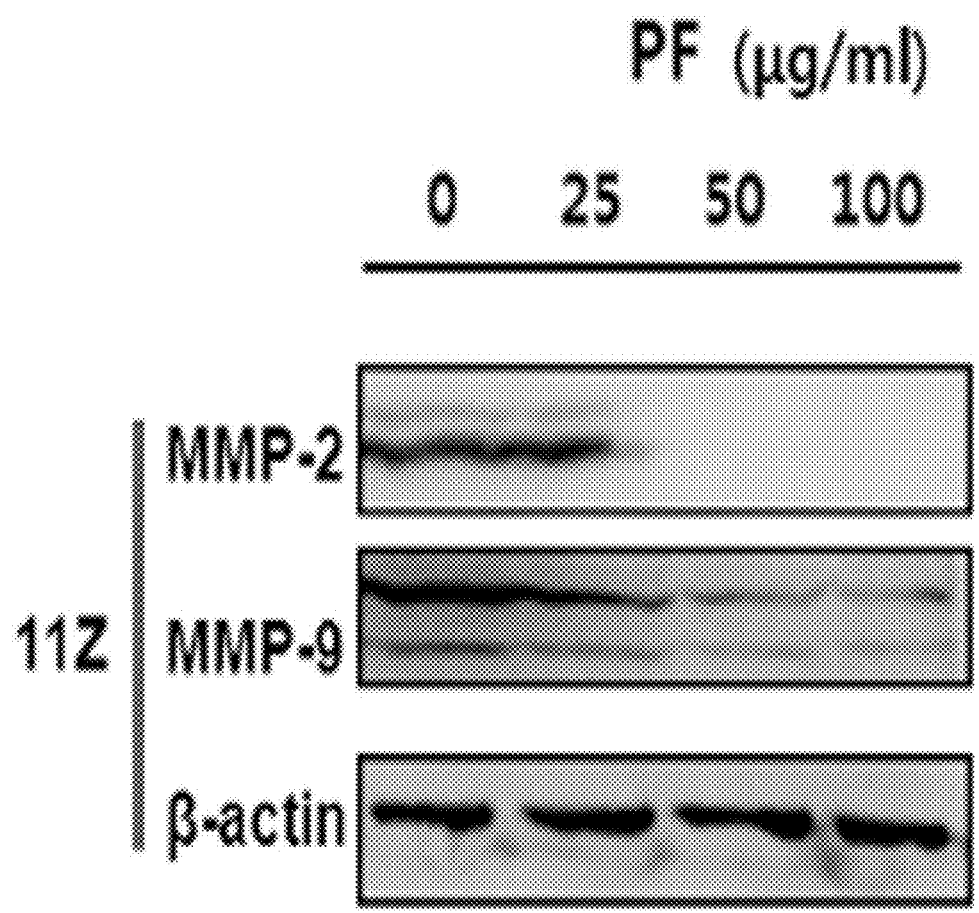
FIG. 13 is a diagram illustrating the expressions of MMP-2 and MMP-9 proteins in the endometriosis cell line 11Z;
PF 0: control;
PF 25: the group treated with 25 ug/ml of Puerariae Flos extract (PF);
PF 50: the group treated with 50 ug/ml of Puerariae Flos extract (PF);
PF 100: the group treated with 100 ug/ml of Puerariae Flos extract (PF); and β-actin: beta actin.
Figure 14:
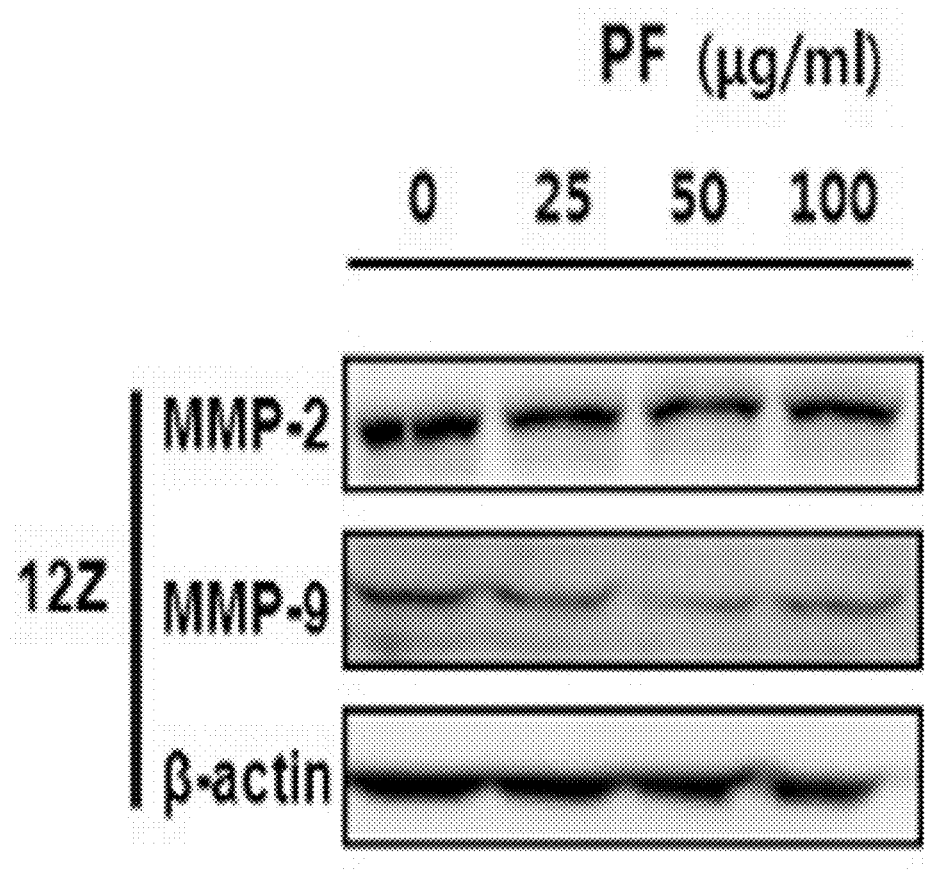
FIG. 14 is a diagram illustrating the expressions of MMP-2 and MMP-9 proteins in the endometriosis cell line 12Z;
PF 0: control;
PF 25: the group treated with 25 ug/ml of Puerariae Flos extract (PF);
PF 50: the group treated with 50 ug/ml of Puerariae Flos extract (PF);
PF 100: the group treated with 100 ug/ml of Puerariae Flos extract (PF); and
β-actin: beta actin.

As a result, it was confirmed that the expressions of MMP-2 and MMP-9 proteins, which are the proteins play an important role in endometriosis cell migration and invasion, were significantly inhibited by Puerariae Flos extract (FIG. 13 and FIG. 14).

Experimental Example 4

Inhibitory Effect of Puerariae Flos Extract on the Expression of COX-2 Involved in Inflammation and Pain To investigate whether or not the Puerariae Flos extract of the present invention could inhibit the expression of COX-2 mRNA known to be involved in pain caused by endometriosis, real-time PCR was performed.

Particularly, the endometriosis cell lines 11Z and 12Z were treated with Puerariae Flos extract at the concentration of 50 ug/ml for 24 hours. Total RNA was extracted from the 11Z and 12Z by the conventional method using TRIzol (Invitrogen Canada, Burlington, ON, Canada) known to those in the art. Reverse transcription polymerase chain reaction (RT-PCR) was performed with the total RNA to obtain the first-strand cDNA. Then, SYBR Green real-time PCR was performed using the first-strand cDNA amplified by PCR as a template with Thermal Cycler Dice Real Time PCR System (Takara, Japan) as follows; denaturation at 95° C. for 5 seconds, annealing at 57° C. for 10 seconds, extension at 72° C. for 20 seconds, 45 cycles from denaturation to extension. COX-2 primers and the control GAPDH primers used in the said SYBR Green real-time PCR are as shown in [Table 2]. The average Ct value of COX-2 was obtained in triplicate and modified by Ct value of the control GAPDH.

TABLE 2

| | | | |
|---|---|---|---|
| COX-2 sense primer | 5'- | CTCCCTTGGGTGTCAAAGGT- 3' | SEQ. ID. NO: 7 |
| antisense primer | 5'- | GTGAAGTGCTGGGCAAAGAA- 3' | SEQ. ID. NO: 8 |
| GAPDH sense primer | 5'- | GAGTCAACGGATTTGGTCGT- 3 | SEQ. ID. NO: 5 |
| antisense primer | 5'- | TTGATTTTGGAGGGATCTCG- 3' | SEQ. ID. NO: 6 |

Figure 15:
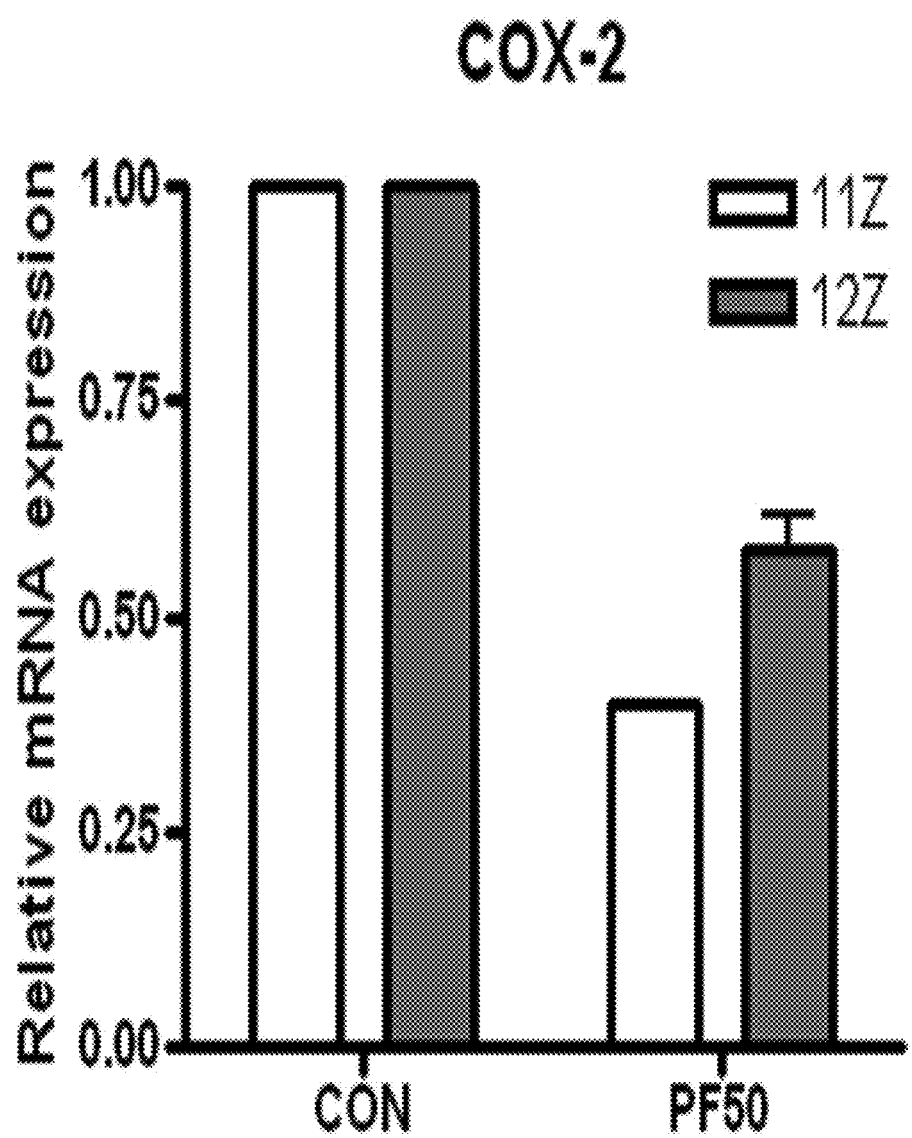
FIG. 15 is a diagram illustrating the expression of COX-2 mRNA in the endometriosis cell lines 11Z and 12Z;
CON: control; and
PF 50: the group treated with 50 ug/ml of Puerariae Flos extract (PF).

As a result, it was confirmed in the endometriosis cell lines 11Z and 12Z that the mRNA expression of COX-2, which is the characteristic enzyme involved in endometriosis mediated pain, was significantly inhibited by Puerariae Flos extract (FIG. 15).

Experimental Example 5

Inhibitory Effect of Puerariae Flos Extract on the Expressions of Inflammatory Cytokines To investigate whether or not the Puerariae Flos extract of the present invention could inhibit the mRNA expressions of inflammatory cytokines known to be over-expressed in endometriosis cells, real-time PCR was performed.

Particularly, the endometriosis cell lines 11Z and 12Z were treated with Puerariae Flos extract at the concentration of 50 ug/ml for 24 hours. Total RNA was extracted from the 11Z and 12Z by the conventional method using TRIzol (Invitrogen Canada, Burlington, ON, Canada) known to those in the art. Reverse transcription polymerase chain reaction (RT-PCR) was performed with the total RNA to obtain the first-strand cDNA. Then, SYBR Green real-time PCR was performed using the first-strand cDNA amplified by PCR as a template with Thermal Cycler Dice Real Time PCR System (Takara, Japan) as follows; denaturation at 95° C. for 5 seconds, annealing at 57° C. for 10 seconds, extension at 72° C. for 20 seconds, 45 cycles from denaturation to extension. MCP-1 primers, RANTES primers, and the control GAPDH primers used in the said SYBR Green real-time PCR are as shown in [Table 3]. The average Ct values of MCP-1 and RANTES were obtained in triplicate and modified by Ct value of the control GAPDH.

TABLE 3

| | | | |
|---|---|---|---|
| MCP-1 | sense primer | 5'-<br>3' | GCTCATAGCAGCCACCTTCA-SEQ. ID.<br>NO: 9 |
| | antisense primer | 5'-<br>3' | GGACACTTGCTGCTGGTGAT-SEQ. ID.<br>NO: 10 |
| RANTES | sense primer | 5'-<br>3' | TCATTGCTACTGCCCTCTGC-SEQ. ID.<br>NO: 11 |
| | antisense primer | 5'-<br>3' | CTTTCGGGTGACAAAGACGA-SEQ. ID.<br>NO: 12 |
| GAPDH | sense primer | 5'-<br>3 | GAGTCAACGGATTTGGTCGT-SEQ. ID.<br>NO: 5 |
| | antisense primer | 5'-<br>3' | TTGATTTTGGAGGGATCTCG-SEQ. ID.<br>NO: 6 |

Figure 16:
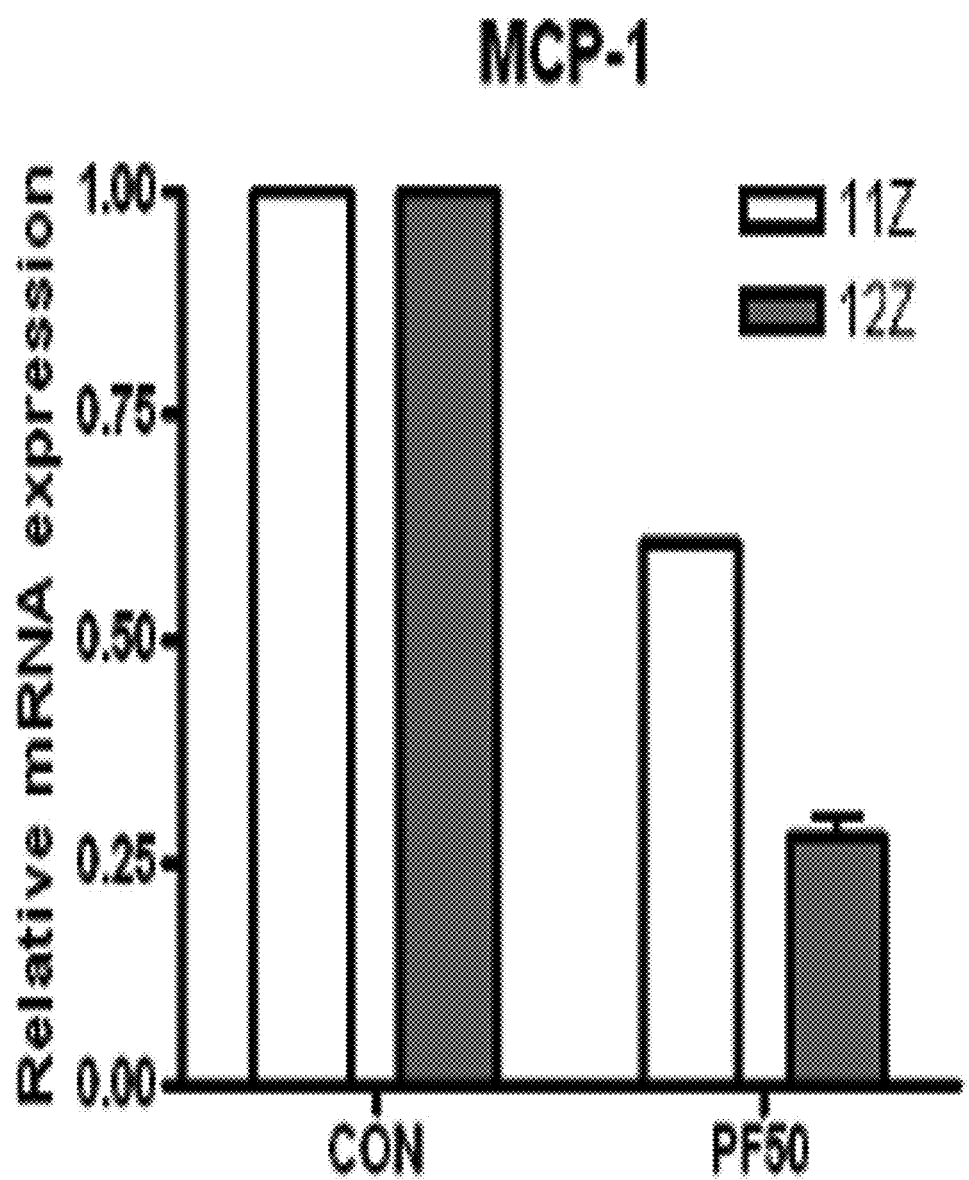
FIG. 16 is a diagram illustrating the expression of MCP-1 mRNA in the endometriosis cell lines 11Z and 12Z;
CON: control; and PF 50: the group treated with 50 ug/ml of Puerariae Flos extract (PF).
Figure 17:
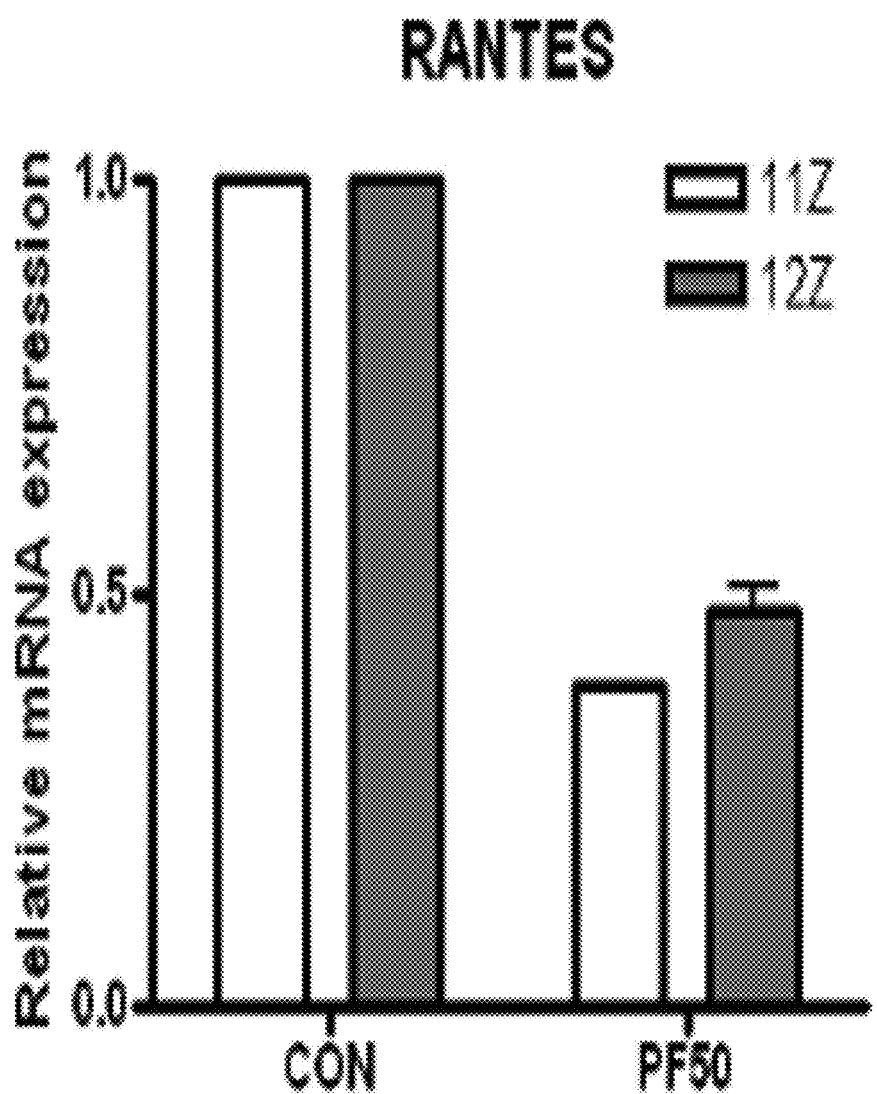
FIG. 17 is a diagram illustrating the expression of RANTES mRNA in the endometriosis cell lines 11Z and 12Z;
CON: control; and
PF 50: the group treated with 50 ug/ml of Puerariae Flos extract (PF).

As a result, it was confirmed in the endometriosis cell lines 11Z and 12Z that the mRNA expressions of MCP-1 and RANSTE, which are the cytokines involved in endometriosis mediated inflammation, were significantly inhibited by Puerariae Flos extract (FIG. 16 and FIG. 17).

Manufacturing Example 1

Preparation of Pharmaceutical Formulations

<1-1> Preparation of Powders

| | |
|---|---|
| Extract of Example 1 | 2 g |
| Lactose | 1 g |

Powders were prepared by mixing all the above components, which were filled in airtight packs according to the conventional method for preparing powders.

<1-2> Preparation of Tablets

| | |
|---|---|
| Extract of Example 1 | 100 mg |
| Corn starch | 100 mg |
| Lactose | 100 mg |
| Magnesium stearate | 2 mg |

Tablets were prepared by mixing all the above components by the conventional method for preparing tablets.

<1-3> Preparation of Capsules

| | |
|---|---|
| Extract of Example 1 | 100 mg |
| Corn starch | 100 mg |
| Lactose | 100 mg |
| Magnesium stearate | 2 mg |

Capsules were prepared by mixing all the above components, which were filled in gelatin capsules according to the conventional method for preparing capsules.

<1-4> Preparation of Pills

| | |
|---|---|
| Extract of Example 1 | 1 g |
| Lactose | 1.5 g |
| Glycerin | 1 g |
| Xylitol | 0.5 g |

Pills were prepared by mixing all the above components according to the conventional method for preparing pills. Each pill contained 4 g of the mixture.

<1-5> Preparation of Granules

| | |
|---|---|
| Extract of Example 1 | 150 mg |
| Soybean extract | 50 mg |
| Glucose | 200 mg |
| Starch | 600 mg |

All the above components were mixed, to which 100 mg of 30% ethanol was added. The mixture was dried at 60° C. and the prepared granules were filled in packs.

Manufacturing Example 2

Preparation of Food

<2-1> Preparation of Flour Food 0.5~5.0 weight part of the extract of Example 1 of the present invention was added to the flour. Health enhancing food such as bread, cake, cookies, crackers and noodles was prepared with the flour mixture according to the conventional method.

<2-2> Preparation of Soups and Gravies 0.1~5.0 weight part of the extract of Example 1 of the present invention was added to soups and gravies. Health enhancing meat products, soups and gravies were prepared with this mixture by the conventional method.

<2-3> Preparation of Ground Beef Health enhancing ground beef was prepared by mixing 10 weight part of the extract of Example 1 of the present invention with ground beef according to the conventional method.

<2-4> Preparation of Dairy Products

5~10 weight part of the extract of Example 1 of the present invention was added to milk. Health enhancing dairy products such as butter and ice cream were prepared with the milk mixture according to the conventional method.

<2-5> Preparation of Sun-Sik

Brown rice, barley, glutinous rice and Yulmu (Job's tears) were gelatinized according to the conventional method, dried and pulverized to obtain 60-mesh powders.

Black soybean, black sesame and wild sesame were steamed and dried according to the conventional method and pulverized to obtain 60-mesh powders.

The extract of Example 1 of the present invention was concentrated under reduced pressure, spray-dried and pulverized to obtain 60-mesh dry powders.

Sun-Sik was prepared by mixing the dry powders of the grains, seeds and the extract of Example 1 of the present invention according to the below ratio.

Grains (brown rice: 30 weight part, Yulmu: 15 weight part, barley: 20 weight part), Seeds (wild sesame: 7 weight part, black soybean: 8 weight part, black sesame: 7 weight part), The extract of Example 1 of the present invention (3 weight part),
*Ganoderma lucidum* (0.5 weight part),
*Rehmannia glutinosa* (0.5 weight part).

Manufacturing Example 3

Preparation of Beverages

<3-1> Preparation of Health Beverages

The extract of Example 1 of the present invention (5 g) was mixed with liquid fructose (0.5%), oligosaccharide (2%), sugar (2%), salt (0.5%), and water (75%). After mixing completely, the mixture was sterilized instantly and filled small containers such as glass bottles, pet bottles, etc, to prepare health beverages.

<3-2> Preparation of Vegetable Juice

Health enhancing vegetable juice was prepared by adding 5 g of the extract of Example 1 of the present invention to 1,000 ml of tomato or carrot juice according to the conventional method.

<3-3> Preparation of Fruit Juice

Health enhancing fruit juice was prepared by adding 1 g of the extract of Example 1 of the present invention to 1,000 ml of apple or grape juice according to the conventional method.

What is claimed is:

1. A method for treating endometriosis which includes the step of administering a pharmaceutically effective dose of Puerariae Flos extract to a subject having endometriosis.

2. The method of claim 1, wherein the Puerariae Flos extract is extracted by using water, a $C_1$~$C_6$ lower alcohol or a mixture thereof as a solvent.

3. The method of claim 2, wherein the lower alcohol is ethanol or methanol.

4. The method of claim 1, wherein the Puerariae Flos extract inhibits the expression of MMP-2, MMP-9, COX-2, MCP-1 or RANTES.

5. The method of claim 1, wherein the Puerariae Flos extract inhibits endometrial cell migration and adhesion.

6. A method for treating a complications of endometriosis which includes the step of administering a pharmaceutically effective dose of Puerariae Flos extract to a subject having a complications of endometriosis, wherein the complication of endometriosis is selected from the group consisting of pelvic inflammatory disease, pelvic adhesion, ectopic pregnancy and infertility.

7. The method of claim 6, wherein the Puerariae Flos extract is extracted by using water, a $C_1$~$C_6$ lower alcohol or a mixture thereof as a solvent.

8. The method of claim 7, wherein the lower alcohol is ethanol or methanol.

9. The method of claim 6, wherein the Puerariae Flos extract inhibits the expression of MMP-2, MMP-9, COX-2, MCP-1 or RANTES.

10. The method of claim 6, wherein the Puerariae Flos extract inhibits endometrial cell migration and adhesion.

11. A method for inhibiting migration and adhesion of an endometrial cell, comprising administering a pharmaceutically effective dose of Puerariae Flos extract to the endometrial cell.

12. The method of claim 11, wherein the Puerariae Flos extract is extracted by using water, a $C_1$~$C_6$ lower alcohol or a mixture thereof as a solvent.

13. The method of claim 12, wherein the lower alcohol is ethanol or methanol.

14. The method of claim 11, wherein the Puerariae Flos extract inhibits the expression of MMP-2, MMP-9, COX-2, MCP-1 or RANTES in the endometrial cell.

* * * * *

UNITED STATES PATENT AND TRADEMARK OFFICE
CERTIFICATE OF CORRECTION

PATENT NO. : 9,504,724 B2
APPLICATION NO. : 14/346667
DATED : November 29, 2016
INVENTOR(S) : Jung-Hye Choi et al.

Page 1 of 1

It is certified that error appears in the above-identified patent and that said Letters Patent is hereby corrected as shown below:

In the Claims

Please correct the error in Claim 6, Line 4 (found in Column 21, Line 28), as follows:
"a complication of endometriosis,"

Signed and Sealed this
Seventh Day of February, 2017

Michelle K. Lee
*Director of the United States Patent and Trademark Office*

```
SEQUENCE LISTING

<160> NUMBER OF SEQ ID NOS: 12

<210> SEQ ID NO 1
<211> LENGTH: 20
<212> TYPE: DNA
<213> ORGANISM: Artificial Sequence
<220> FEATURE:
<223> OTHER INFORMATION: MMP-2 sense primer

<400> SEQUENCE: 1
accgcgacaa gaagtatggc                                                   20

<210> SEQ ID NO 2
<211> LENGTH: 20
<212> TYPE: DNA
<213> ORGANISM: Artificial Sequence
<220> FEATURE:
<223> OTHER INFORMATION: MMP-2 anti-sense primer

<400> SEQUENCE: 2
ccacttgcgg tcatcatcgt                                                   20

<210> SEQ ID NO 3
<211> LENGTH: 20
<212> TYPE: DNA
<213> ORGANISM: Artificial Sequence
<220> FEATURE:
<223> OTHER INFORMATION: MMP-9 sense primer

<400> SEQUENCE: 3
cgatgacgag ttgtggtccc                                                   20

<210> SEQ ID NO 4
<211> LENGTH: 20
<212> TYPE: DNA
<213> ORGANISM: Artificial Sequence
<220> FEATURE:
<223> OTHER INFORMATION: MMP-9 anti-sense primer

<400> SEQUENCE: 4
tcgtagttgg ccgtggtact                                                   20

<210> SEQ ID NO 5
<211> LENGTH: 20
<212> TYPE: DNA
<213> ORGANISM: Artificial Sequence
<220> FEATURE:
<223> OTHER INFORMATION: GAPDH sense primer

<400> SEQUENCE: 5
gagtcaacgg atttggtcgt                                                   20
```

```
<210> SEQ ID NO 6
<211> LENGTH: 20
<212> TYPE: DNA
<213> ORGANISM: Artificial Sequence
<220> FEATURE:
<223> OTHER INFORMATION: GAPDH anti-sense primer

<400> SEQUENCE: 6
ttgattttgg agggatctcg                                           20

<210> SEQ ID NO 7
<211> LENGTH: 20
<212> TYPE: DNA
<213> ORGANISM: Artificial Sequence
<220> FEATURE:
<223> OTHER INFORMATION: COX-2 sense primer

<400> SEQUENCE: 7
ctcccttggg tgtcaaaggt                                           20

<210> SEQ ID NO 8
<211> LENGTH: 20
<212> TYPE: DNA
<213> ORGANISM: Artificial Sequence
<220> FEATURE:
<223> OTHER INFORMATION: COX-2 anti-sense primer

<400> SEQUENCE: 8
gtgaagtgct gggcaaagaa                                           20

<210> SEQ ID NO 9
<211> LENGTH: 20
<212> TYPE: DNA
<213> ORGANISM: Artificial Sequence
<220> FEATURE:
<223> OTHER INFORMATION: MCP-1 sense primer

<400> SEQUENCE: 9
gctcatagca gccaccttca                                           20

<210> SEQ ID NO 10
<211> LENGTH: 20
<212> TYPE: DNA
<213> ORGANISM: Artificial Sequence
<220> FEATURE:
<223> OTHER INFORMATION: MCP-1 anti-sense primer

<400> SEQUENCE: 10
ggacacttgc tgctggtgat                                           20

<210> SEQ ID NO 11
<211> LENGTH: 20
<212> TYPE: DNA
<213> ORGANISM: Artificial Sequence
<220> FEATURE:
<223> OTHER INFORMATION: RANTES sense primer

<400> SEQUENCE: 11
tcattgctac tgccctctgc                                           20

<210> SEQ ID NO 12
<211> LENGTH: 20
<212> TYPE: DNA
<213> ORGANISM: Artificial Sequence
```

```
<220> FEATURE:
<223> OTHER INFORMATION: RANTES anti-sense primer

<400> SEQUENCE: 12
ctttcgggtg acaaagacga                                              20
```